(12) United States Patent
Pommier et al.

(10) Patent No.: US 8,865,686 B2
(45) Date of Patent: Oct. 21, 2014

(54) TETRACYCLINE COMPOUNDS AS TYROSYL-DNA PHOSPHODIESTERASE I INHIBITORS

(75) Inventors: Yves Pommier, Bethesda, MD (US); Laurent Thibaut, Yerres (FR); Christophe Marchand, Gaithersburg, MD (US)

(73) Assignee: The United States of America, as Represented by the Secretary, Dept. of Health and Human Services, Washington, DC (US)

( * ) Notice: Subject to any disclaimer, the term of this patent is extended or adjusted under 35 U.S.C. 154(b) by 1090 days.

(21) Appl. No.: 12/241,011

(22) Filed: Sep. 29, 2008

(65) Prior Publication Data

US 2009/0176747 A1 Jul. 9, 2009

Related U.S. Application Data

(63) Continuation-in-part of application No. PCT/US2007/007724, filed on Mar. 27, 2007.

(60) Provisional application No. 60/786,746, filed on Mar. 27, 2006.

(51) Int. Cl.
| | | |
|---|---|---|
| *A61K 31/65* | (2006.01) | |
| *A61P 35/00* | (2006.01) | |
| *C07D 499/21* | (2006.01) | |
| *C07C 237/26* | (2006.01) | |
| *C07D 295/13* | (2006.01) | |

(52) U.S. Cl.
CPC .............. *A61K 31/65* (2013.01); *C07C 237/26* (2013.01); *C07D 499/21* (2013.01); *C07D 295/13* (2013.01)
USPC ............................ 514/152; 514/154; 540/304

(58) Field of Classification Search
CPC .. A61K 31/65; C07C 237/26; C07C 2103/46; C07D 295/13; C07D 499/21
USPC ................................. 514/152, 154; 540/304
See application file for complete search history.

(56) References Cited

FOREIGN PATENT DOCUMENTS

| | | | |
|---|---|---|---|
| WO | 2005082860 A1 | 9/2005 | |
| WO | WO 2006/099095 | * 3/2006 | ............. A61K 44/00 |

OTHER PUBLICATIONS

Barthelmes et al. (The Journal of Biological chemistry, vol. 279 (53), 2004, pp. 55618-55625.*
International Search Report; International Application No. PCT/US2007/007724; International Filing Date Mar. 27, 2007; 3 pages.
Sagun KC et al., "Antioxidants prevent oxidative DNA damage and cellular transformation elicited by the overexpression of c-MYC", Mutat.Res. (2006) 29 593(1-2): 64-79.
Peter A. Cerutti, "Prooxidant States and Tumor Promotion", (1985) Science 227 (4685):375-381.
Vafa et al., "c-Myc Can Induce DNA Damage, Increase Reactive Oxygen Species, and Mitigate p53 Function: A Mechanism for Oncogene-Induced Genetic Instability", (2002) Mol Cell 9(5):1031-1044.

* cited by examiner

*Primary Examiner* — Savitha Rao
(74) *Attorney, Agent, or Firm* — Cantor Colburn LLP

(57) ABSTRACT

The instant invention is directed towards tetracycline compositions, and methods of inhibiting Tdp1 activity, and methods of treating Tdp1-associated disorders.

8 Claims, 12 Drawing Sheets

TETRACYCLINE COMPOUNDS AS TYROSYL-DNA PHOSPHODIESTERASE I INHIBITORS

The present application is a continuation-in-part of PCT International Application PCT/US2007/007724, filed Mar. 27, 2007, which claims the benefit of U.S. provisional application 60/786,746, filed Mar. 27, 2006, both of which applications are incorporated herein by reference in their entirety.

STATEMENT OF GOVERNMENTAL INTEREST

This invention was funded by the National Cancer Institute at the National Institutes of Health. The United States Government has certain rights in this invention.

BACKGROUND

Cancer, in all its manifestations, remains a devastating disorder. Although cancer is commonly considered to be a single disease, it actually comprises a family of diseases wherein normal cell differentiation is modified so that it becomes abnormal and uncontrolled. As a result, these malignant cells rapidly proliferate. Eventually, the cells spread or metastasize from their origin and colonize other organs, eventually killing their host. Due to the wide variety of cancers presently observed, numerous strategies have been developed to destroy cancer within the body.

Typically, cancer is treated by chemotherapy, in which highly toxic chemicals are given to the patient, or by radiotherapy, in which toxic doses of radiation are directed at the patient. Unfortunately, these "cytotoxic" treatments also kill extraordinary numbers of healthy cells, causing the patient to experience acute debilitating symptoms including nausea, diarrhea, hypersensitivity to light, hair loss, etc. The side effects of these cytotoxic compounds limits the frequency and dosage at which they can be administered. Such disabling side effects can be mitigated to some degree by using compounds that selectively target cycling cells, i.e., interfering with DNA replication or other growth processes in cells that are actively reproducing. Since cancer cells are characterized by their extraordinary ability to proliferate, such protocols preferentially kill a larger proportion of cancer cells in comparison to healthy cells, but cytotoxicity and ancillary sickness remains a problem.

Another strategy for controlling cancer involves the use of signal transduction pathways in malignant cells to "turn off" their uncontrolled proliferation, or alternatively, instruct such cells to undergo apoptosis. Such methods of treating cancer are promising but a substantial amount of research is needed in order to make these methods viable alternatives.

The treatment and/or cure of cancer has been intensely investigated culminating in a wide range of therapies. Cancer has been typically treated with surgery, radiation and chemotherapy, alone or in conjunction with various therapies employing drugs, biologic agents, antibodies, and radioactive immunoconjugates, among others. The common goal of cancer treatment has been, and continues to be, the elimination or amelioration of cancerous tumors and cells with minimal unpleasant or life-threatening side effects, due to toxicity to normal tissues and cells. However, despite efforts, these goals remain largely unmet.

Tetracycline and a number of its chemical relatives have been used as antibiotics. The parent compound, tetracycline, has the following general structure:

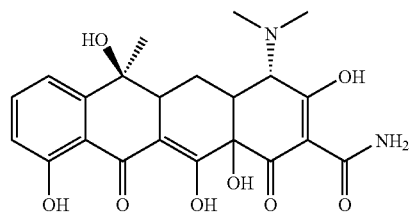 [SMILES: CN(C)[C@@H]1C(O)=C(C(N)=O)C(=O)C2(O)C(O)=C3C(=O)c4c(O)cccc4[C@@](C)(O)C3CC12]

The numbering system for the multiple ring nucleus is as follows:

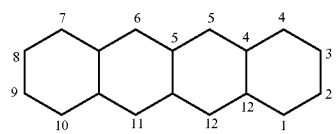

Tetracycline, as well as the 5-OH (terramycin) and 7-Cl (aureomycin) derivatives, exist in nature, and are all well known antibiotics. Semisynthetic derivatives such as 7-dimethylamino-tetracycline (minocycline) and 6α-deoxy-5-hydroxy-tetracycline (doxycycline) are also known antibiotics. However, changes to the basic structure of the ring system, or replacement of substituents at positions 1-4 or 10-12, generally lead to synthetic tetracyclines with substantially less, or essentially no, antibacterial activity. For example, 4-de(dimethylamino)tetracycline is commonly considered to be a non-antibacterial tetracycline.

Tetracycline compounds affect protein synthesis and appear to have anti-inflammatory properties in addition to their anti-microbial properties which are useful for treatment of arthritis. The anti-inflammatory activity of tetracycline compounds make them useful for treating other inflammatory disorders, even in the absence of an infectious agent. Tetracycline compounds can inhibit enzymes associated with inflammatory diseases such as matrix metalloproteases (MMPs), collagenase, gelatinase and elastase. While it is widely thought that tetracycline compounds decrease enzyme activity by chelation, they may also decrease inflammation by decreasing production of proinflammatory or other compounds. Tetracycline compounds may be effective when used with other compounds in the treatment of inflammatory conditions.

More recently, it has been established that tetracyclines, which are rapidly absorbed and have a prolonged plasma half-life, exert biological effects independent of their antimicrobial activity (Golub et al. 1991, Golub et al. 1992, Uitto et al. 1994). Such effects include inhibition of matrix metalloproteinases (abbreviated "MMPs"), including collagenases (MMP-1; MMP-8; MMP-13) and gelatinases (MMP-2; MMP-9), as well as prevention of pathologic tissue destruction (Golub et al. 1991).

In view of the above considerations, it is clear that there is a need to supplement existing methods of inhibiting cancer cell invasiveness and metastasis. Current approaches rely on highly cytotoxic compounds that cause ancillary debilitating sickness in patients, or use methodology that is expensive, procedurally difficult, and unpredictable.

BRIEF SUMMARY OF THE INVENTION

Accordingly, it is one of the purposes of this invention to overcome the above limitations in cancer treatment, by providing a compound and method for inhibiting the growth processes characteristic of cancer cells, including inhibiting invasiveness and metastasis, as well as inducing regression of primary tumors. In particular, it is desirable to identify anticancer compounds and methods that inhibit cancer growth specifically and with relatively high activity, i.e., being active at doses that are substantially free of harmful side effects. Additionally, it is a purpose of the invention to provide methods and compositions suitable for the development, identification, and/or characterization of compounds that are capable of modulating the activity of tyrosyl-DNA phosphodiesterases (TDPs), particularly tyrosyl-DNA phosphodiesterase 1 (TDP1). The present invention provides means to identify and characterize compounds that are suitable for inhibiting TDP activity in vivo and in vitro.

In certain aspects, the invention provides a method of inhibiting Tdp1 activity in a subject, the method comprising administering to the subject a tetracycline compound capable of modulating the activity of Tdp1. In one embodiment, the invention provides a method of inhibiting Tdp1 activity, wherein the tetracycline compound is a compound of formula I:

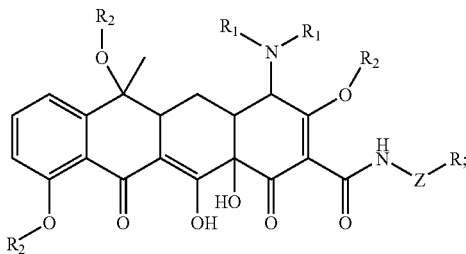

wherein,

Z is $S(O)$, $S(O)_2$, $N(R^b)$, $C(O)$, $C(S)$, $C(S)NR^b$, $C(NR)$, $C(NR)NR^b$, $C(O)NR^b$, $C(O)O$, $(C(R^a)(R^b))_m$, $(C(R^a)(R^b))_mNR^b$, $(C(R^a)(R^b))_mO$, $(C(R^a)(R^b))_mS(O)_p$, $NR^bC(O)NR^b$, $NR^bC(S)NR^b$, $NR^bC(O)$, $NR^bC(O)O$, $NR^bC(NR)NR^b$, $NR^bC(S)O$, $NR^bS(O)_pNR^b$, $C(NR)O$, $S(O)_pNR^b$, or absent;

each $R_1$ and $R_2$ is independently H, alkyl, cycloalkyl, heterocycloalkyl, aryl, heteroaryl, aralkyl, heteroaralkyl, hydroxylalkyl, —$C(O)R^a$, —$C(S)R^a$, —$C(NR)R^a$, haloalkyl, —$S(O)R^a$, —$S(O)_2R^a$, —$P(O)R^aR^a$, —$P(S)R^aR^a$, or alkylcarbonylalkyl; each of which may be optionally substituted;

R is H, alkyl, alkylcarbonyl, —$OR^b$, —$SR^b$, —$NR^aR^a$, hydroxylalkyl, —$C(O)R^a$, —$OC(O)R^a$, —$SC(O)R^a$, —$NR^bC(O)R^a$, —$C(S)R^a$, —$OC(S)R^a$, —$SC(S)R^a$, —$NR^bC(S)R^a$, —$C(NR)R^a$, —$OC(NR)R^a$, —$SC(NR)R^a$, —$NR^bC(NR)R^a$, —$SO_2R^a$, —$S(O)R^a$, —$NR^bSO_2R^a$, —$OS(O)_2R^a$, —$OP(O)R^aR^a$, —$P(O)R^aR^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each $R^a$ is independently, H, alkyl, alkenyl, alkynyl, cycloalkyl, heterocycloalkyl, aralkyl, heteroaralkyl, aryl, heteroaryl, haloalkyl, —$OR^b$, —$SR^b$, —$NR^aR^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more $R^a$ groups, when attached to a heteroatom, may together form a heterocyclic ring with said heteroatom, wherein the heterocyclic ring may be optionally substituted;

each $R^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and
each p is independently 0, 1, or 2.

In another embodiment, the invention provides a method of inhibiting Tdp1 activity, wherein the tetracycline compound is a compound of formula Ia:

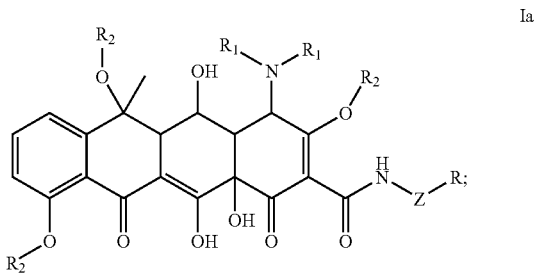

wherein,

Z is $S(O)$, $S(O)_2$, $N(R^b)$, $C(O)$, $C(S)$, $C(S)NR^b$, $C(NR)$, $C(NR)NR^b$, $C(O)NR^b$, $C(O)O$, $(C(R^a)(R^b))_m$, $(C(R^a)(R^b))_mNR^b$, $(C(R^a)(R^b))_mO$, $(C(R^a)(R^b))_mS(O)_p$, $NR^bC(O)NR^b$, $NR^bC(S)NR^b$, $NR^bC(O)$, $NR^bC(O)O$, $NR^bC(NR)NR^b$, $NR^bC(S)O$, $NR^bS(O)_pNR^b$, $C(NR)O$, $S(O)_pNR^b$, or absent;

each $R_1$ and $R_2$ is independently H, alkyl, cycloalkyl, heterocycloalkyl, aryl, heteroaryl, aralkyl, heteroaralkyl, hydroxylalkyl, —$C(O)R^a$, —$C(S)R^a$, —$C(NR)R^a$, haloalkyl, —$S(O)R^a$, —$S(O)_2R^a$, —$P(O)R^aR^a$, —$P(S)R^aR^a$, or alkylcarbonylalkyl; each of which may be optionally substituted;

R is H, alkyl, alkylcarbonyl, —$OR^b$, —$SR^b$, —$NR^aR^a$, hydroxylalkyl, —$C(O)R^a$, —$OC(O)R^a$, —$SC(O)R^a$, —$NR^bC(O)R^a$, —$C(S)R^a$, —$OC(S)R^a$, —$SC(S)R^a$, —$NR^bC(S)R^a$, —$C(NR)R^a$, —$OC(NR)R^a$, —$SC(NR)R^a$, —$NR^bC(NR)R^a$, —$SO_2R^a$, —$S(O)R^a$, —$NR^bSO_2R^a$, —$OS(O)_2R^a$, —$OP(O)R^aR^a$, —$P(O)R^aR^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each $R^a$ is independently, H, alkyl, alkenyl, alkynyl, cycloalkyl, heterocycloalkyl, aralkyl, heteroaralkyl, aryl, heteroaryl, haloalkyl, —$OR^b$, —$SR^b$, —$NR^aR^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more $R^a$ groups, when attached to a heteroatom, may together form a heterocyclic ring with said heteroatom, wherein the heterocyclic ring may be optionally substituted;

each $R^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and
each p is independently 0, 1, or 2.

In other aspects, the invention provides a method of inhibiting Tdp1 activity in a subject identified as being in need of such treatment, the method comprising administering to the subject a tetracycline compound, wherein the tetracycline compound is capable of binding to Tdp1.

In another aspect, the invention provides a method of treating a Tdp1-related disorder in a subject, comprising administering to said subject in need thereof, an effective amount of a compound of formula I or Ia, such that said subject is treated for said disorder;

wherein the disorder is cancer, tumor, neoplasm, neovascularization, vascularization, cardiovascular disease, intravasation, extravasation, metastasis, arthritis, infection, Alzheimer's Disease, blood clot, atherosclerosis, melanoma, skin disorder, rheumatoid arthritis, diabetic retinopathy, macular edema, or macular degeneration, inflammatory and arthritic disease, or osteosarcoma.

In one aspect, the invention provides a method of treating cancer in a subject identified as in need of such treatment, the method comprising administering to said subject an effective amount of a compound of Formula I:

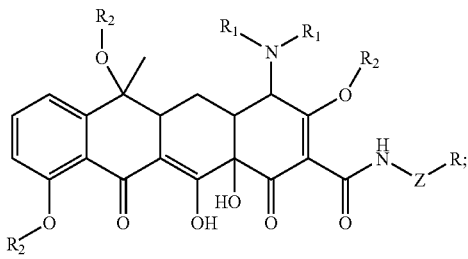

I wherein,

Z is $S(O)$, $S(O)_2$, $N(R^b)$, $C(O)$, $C(S)$, $C(S)NR^b$, $C(NR)$, $C(NR)NR^b$, $C(O)NR^b$, $C(O)O$, $(C(R^a)(R^b))_m$, $(C(R^a)(R^b))_m NR^b$, $(C(R^a)(R^b))_m O$, $(C(R^a)(R^b))_m S(O)_p$, $NR^b C(O)NR^b$, $NR^b C(S)NR^b$, $NR^b C(O)$, $NR^b C(O)O$, $NR^b C(NR)NR^b$, $NR^b C(S)O$, $NR^b S(O)_p NR^b$, $C(NR)O$, $S(O)_p NR^b$, or absent;

each $R_1$ and $R_2$ is independently H, alkyl, cycloalkyl, heterocycloalkyl, aryl, heteroaryl, aralkyl, heteroaralkyl, hydroxylalkyl, —$C(O)R^a$, —$C(S)R^a$, —$C(NR)R^a$, haloalkyl, —$S(O)R^a$, —$S(O)_2R^a$, —$P(O)R^aR^a$, —$P(S)R^aR^a$, or alkylcarbonylalkyl; each of which may be optionally substituted;

R is H, alkyl, alkylcarbonyl, —$OR^b$, —$SR^b$, —$NR^aR^a$, hydroxylalkyl, —$C(O)R^a$, —$OC(O)R^a$, —$SC(O)R^a$, —$NR^bC(O)R^a$, —$C(S)R^a$, —$OC(S)R^a$, —$SC(S)R^a$, —$NR^bC(S)R^a$, —$C(NR)R^a$, —$OC(NR)R^a$, —$SC(NR)R^a$, —$NR^bC(NR)R^a$, —$SO_2R^a$, —$S(O)R^a$, —$NR^bSO_2R^a$, —$OS(O)_2R^a$, —$OP(O)R^aR^a$, —$P(O)R^aR^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each $R^a$ is independently, H, alkyl, alkenyl, alkynyl, cycloalkyl, heterocycloalkyl, aralkyl, heteroaralkyl, aryl, heteroaryl, haloalkyl, —$OR^b$, —$SR^b$, —$NR^bR^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more $R^a$ groups, when attached to a heteroatom, may together form a heterocyclic ring with said heteroatom, wherein the heterocyclic ring may be optionally substituted;

each $R^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In another aspect, the invention provides a method of treating cancer in a subject identified as in need of such treatment, the method comprising administering to said subject an effective amount of a compound of formula Ia:

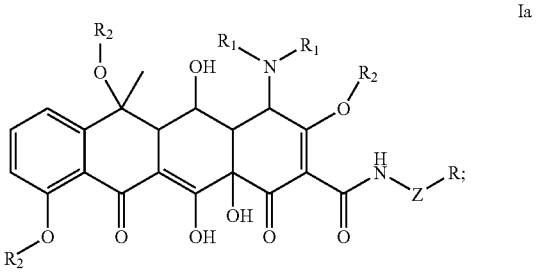

Ia wherein,

Z is $S(O)$, $S(O)_2$, $N(R^b)$, $C(O)$, $C(S)$, $C(S)NR^b$, $C(NR)$, $C(NR)NR^b$, $C(O)NR^b$, $C(O)O$, $(C(R^a)(R^b))_m$, $(C(R^a)(R^b))_m NR^b$, $(C(R^a)(R^b))_m O$, $(C(R^a)(R^b))_m S(O)_p$, $NR^b C(O)NR^b$, $NR^b C(S)NR^b$, $NR^b C(O)$, $NR^b C(O)O$, $NR^b C(NR)NR^b$, $NR^b C(S)O$, $NR^b S(O)_p NR^b$, $C(NR)O$, $S(O)_p NR^b$, or absent;

each $R_1$ and $R_2$ is independently H, alkyl, cycloalkyl, heterocycloalkyl, aryl, heteroaryl, aralkyl, heteroaralkyl, hydroxylalkyl, —$C(O)R^a$, —$C(S)R^a$, —$C(NR)R^a$, haloalkyl, —$S(O)R^a$, —$S(O)_2R^a$, —$P(O)R^aR^a$, —$P(S)R^aR^a$, or alkylcarbonylalkyl; each of which may be optionally substituted;

R is H, alkyl, alkylcarbonyl, —$OR^b$, —$SR^b$, —$NR^aR^a$, hydroxylalkyl, —$C(O)R^a$, —$OC(O)R^a$, —$SC(O)R^a$, —$NR^bC(O)R^a$, —$C(S)R^a$, —$OC(S)R^a$, —$SC(S)R^a$, —$NR^bC(S)R^a$, —$C(NR)R^a$, —$OC(NR)R^a$, —$SC(NR)R^a$, —$NR^bC(NR)R^a$, —$SO_2R^a$, —$S(O)R^a$, —$NR^bSO_2R^a$, —$OS(O)_2R^a$, —$OP(O)R^aR^a$, —$P(O)R^aR^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each $R^a$ is independently, H, alkyl, alkenyl, alkynyl, cycloalkyl, heterocycloalkyl, aralkyl, heteroaralkyl, aryl, heteroaryl, haloalkyl, —$OR^b$, —$SR^b$, —$NR^bR^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more $R^a$ groups, when attached to a heteroatom, may together form a heterocyclic ring with said heteroatom, wherein the heterocyclic ring may be optionally substituted;

each $R^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In another aspect, the invention provides for the use of a tetracycline compound in the manufacture of a medicament for inhibiting or reducing cancer in a patient, the compound being of formula I:

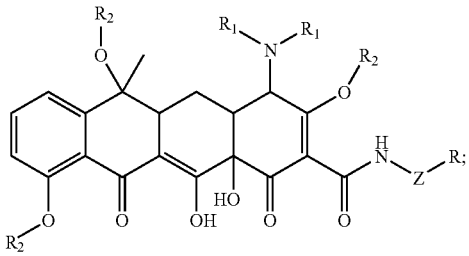

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^x$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In another aspect, the invention provides for the use of a tetracycline compound in the manufacture of a medicament for inhibiting or reducing cancer in a patient, the compound being of formula Ia:

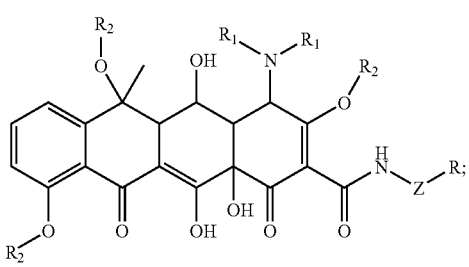

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, In a further aspect, the invention provides a tetracycline compound of formula I:

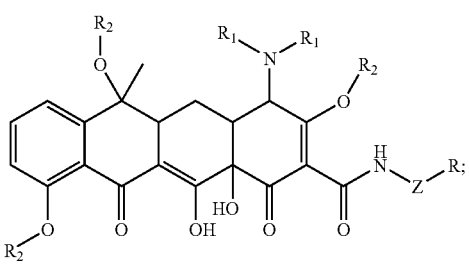

—NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In a further aspect, the invention provides a tetracycline compound of formula Ia:

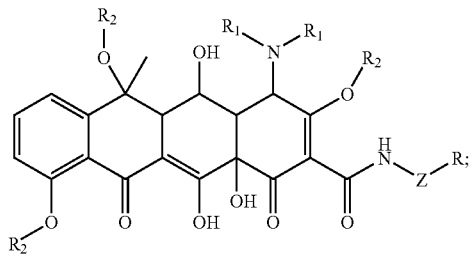

Ia wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In certain aspects, the invention provides for a pharmaceutical composition comprising a compound of Formula I:

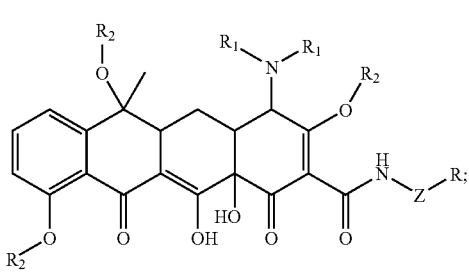

I wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2; together with a pharmaceutically-acceptable carrier or excipient.

In certain aspects, the invention provides for a pharmaceutical composition comprising a compound of Formula Ia:

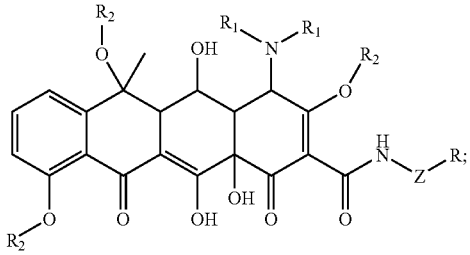

Ia wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2;

together with a pharmaceutically-acceptable carrier or excipient.

In another aspect, the invention provides for a kit comprising an effective amount of a tetracycline compound in unit dosage form, together with instructions for administering the tetracycline compound to a subject suffering from cancer, wherein the compound is compound of formula I:

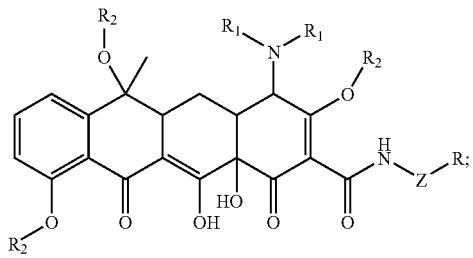

I wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In another aspect, the invention provides for a kit comprising an effective amount of a tetracycline compound in unit dosage form, together with instructions for administering the tetracycline compound to a subject suffering from cancer, wherein the compound is compound of formula Ia:

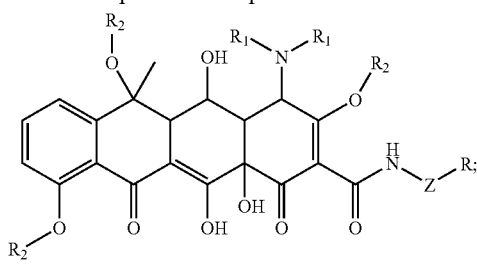

Ia wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$)$_m$S(O)$_p$, NR$^b$C(O)

NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

DETAILED DESCRIPTION

Definitions

Figure 1A:
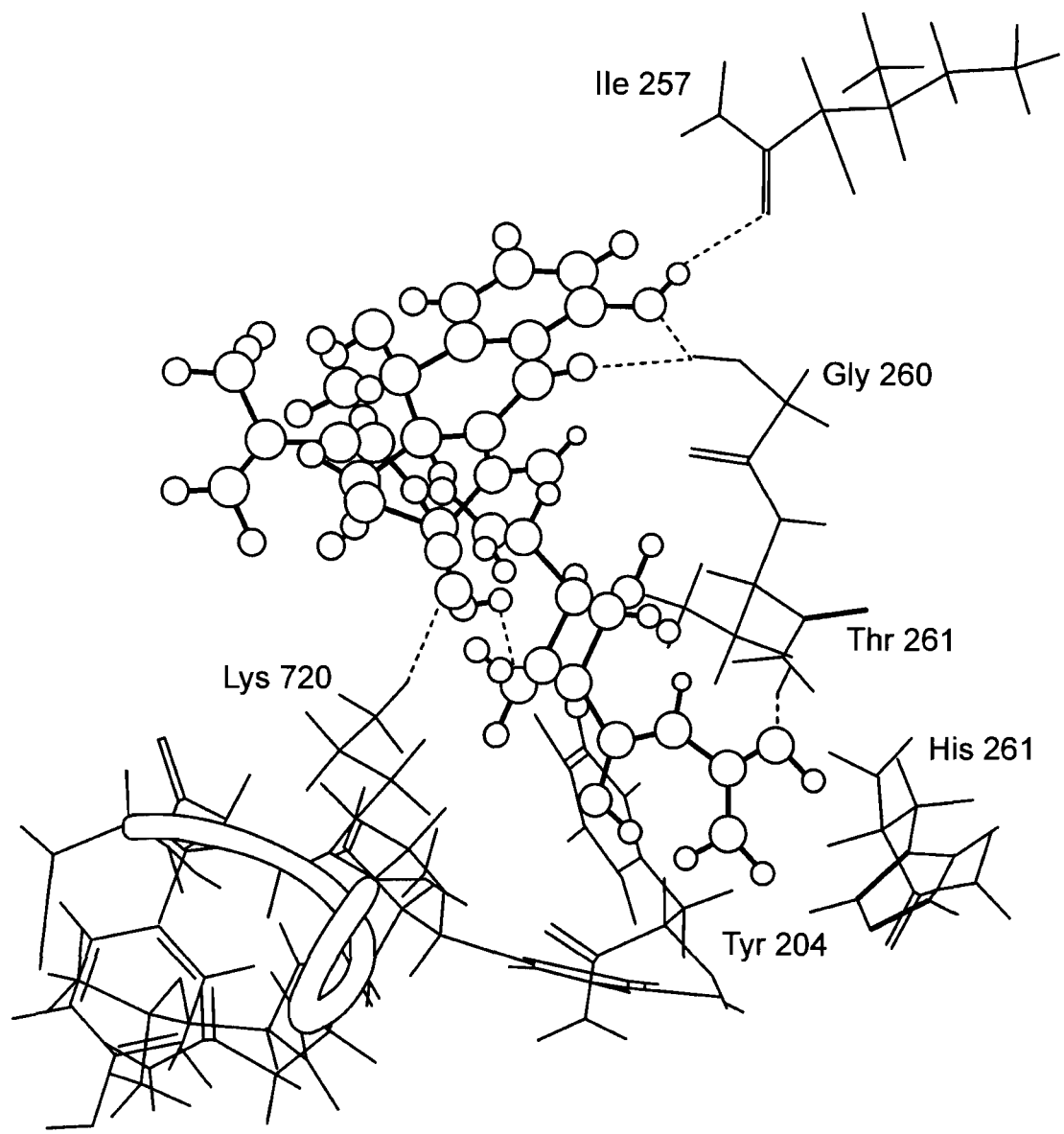
FIG. 1 shows Compounds (a) and (b) (see Example 2) (1RFF) (shown in ball-and stick) docked in the binding site of the Tdp1 N domain. Hydrogen bonds are represented as dashed orange lines and contacts as dashed green lines. For clarity, only important residues and atoms are shown. Color codes used: nitrogen—blue, oxygen—red, carbon—black, hydrogen—grey, protein—blue tube, His 263—red.

In order that the invention may be more readily understood, certain terms are first defined and collected here for convenience.

The term "administration" or "administering" includes routes of introducing the compound(s) to a subject to perform their intended function. Examples of routes of administration which can be used include injection (subcutaneous, intravenous, parenterally, intraperitoneally, intrathecal), oral, inhalation, rectal and transdermal.

The term "admixture" refers to something that is produced from mixing.

The term "alkyl" refers to the radical of saturated aliphatic groups, including straight-chain alkyl groups and branched-chain alkyl groups. The term alkyl further includes alkyl groups, which can further include oxygen, nitrogen, sulfur or phosphorous atoms replacing one or more carbons of the hydrocarbon backbone. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain.

The terms "alkylaryl" or "aralkyl" are used interchangeably, and refer to an alkyl substituted with an aryl (e.g., phenylmethyl (benzyl)), or an aryl group substituted with an alkyl. The term "heteroaralkyl" refers to either an alkylaryl or aralkyl groups that is substituted at any number of positions with a heteroatom.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively.

The term "aryl" as used herein, refers to the radical of aryl groups, including 5- and 6-membered single-ring aromatic groups. "Heteroaryl" groups may include from one to four heteroatoms. Examples of aryl and heteroaryl groups include benzene, pyrrole, furan, thiophene, imidazole, benzoxazole, benzothiazole, triazole, tetrazole, pyrazole, pyridine, pyrazine, pyridazine and pyrimidine, and the like. Polycyclic fused aromatic groups such as naphthyl, quinolyl, indolyl, and the like are also contemplated.

Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" includes all genomic and non-genomic activities elicited by these compounds.

The term "cancer" refers to a malignant tumor of potentially unlimited growth that expands locally by invasion and systemically by metastasis. The term "cancer" also refers to the uncontrolled growth of abnormal cells. Specific cancers are selected from, but not limited to, rhabdomyosarcomas, chorio carcinomas, glioblastoma multiformas (brain tumors), bowel and gastric carcinomas, leukemias, ovarian cancers, prostate cancers, lymphomas, osteosarcomas or cancers which have metastasized.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "chiral" refers to molecules which have the property of non-superimposability of the mirror image partner, while the term "achiral" refers to molecules which are superimposable on their mirror image partner.

The term "cycloalkyl" refers to the radical of saturated or unsaturated cyclic aliphatic groups, including cycloalkyl (alicyclic) groups, alkyl substituted cycloalkyl groups, and cycloalkyl substituted alkyl groups. The term cycloalkyl further includes cycloalkyl groups, which can further include oxygen, nitrogen, sulfur or phosphorous atoms replacing one or more carbons of the hydrocarbon backbone. Preferred cycloalkyls have from 3-10 carbon atoms in their ring structure, and more preferably have 3, 4, 5, 6 or 7 carbons in the ring structure.

The term "diastereomers" refers to stereoisomers with two or more centers of dissymmetry and whose molecules are not mirror images of one another.

The term "deuteroalkyl" refers to alkyl groups in which one or more of the of the hydrogens has been replaced with deuterium.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the angiogenesis inhibitor compound are outweighed by the therapeutically beneficial effects.

A therapeutically effective amount of compound (i.e., an effective dosage) may range from about 0.001 µg/kg/day to about 500 mg/kg/day, preferably 0.01 µg/kg/day and 100 mg/kg/day. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. It will also be appreciated that the effective dosage of a compound used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heterocycloalkyl" refers to the radical of saturated or unsaturated cyclic aliphatic groups substituted by any number of heteroatoms, including heterocycloalkyl (alicyclic) groups, alkyl substituted heterocycloalkyl groups, and heterocycloalkyl substituted alkyl groups. Heteroatoms include but are not limited to oxygen, nitrogen, sulfur or phosphorous atoms replacing one or more carbons of the hydrocarbon backbone. Preferred heterocycloalkyls have from 3-10 carbon atoms in their ring structure, and more preferably have 3, 4, 5, 6 or 7 carbons in the ring structure, wherein a heteroatom may replace a carbon atom.

The terms "hyperproliferative" and "neoplastic" are used interchangeably, and include those cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "inhibition" and "inhibits" refer to a method of prohibiting a specific action or function.

The term "inhibitor," as used herein, refer to a molecule, compound or complex which blocks or modulates a biological or immunological activity.

The term "isomers" or "stereoisomers" refers to compounds which have identical chemical constitution, but differ with regard to the arrangement of the atoms or groups in space.

The term "leukemia" is intended to have its clinical meaning, namely, a neoplastic disease in which white corpuscle maturation is arrested at a primitive stage of cell development. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

The term "leukemic cancer" refers to all cancers or neoplasias of the hemopoietic and immune systems (blood and lymphatic system). Chronic myelogenous leukemia (CML), also known as chronic granulocytic leukemia (CGL), is a neoplastic disorder of the hematopoietic stem cell.

The term "modulate" refers to increases or decreases in the activity of a cell in response to exposure to a compound of the invention, e.g., the inhibition of proliferation and/or induction of differentiation of at least a sub-population of cells in an animal such that a desired end result is achieved, e.g., a therapeutic result. In preferred embodiments, this phrase is intended to include hyperactive conditions that result in pathological disorders.

The term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangably, as their context will reveal, referring to generally to cells experiencing abnormal cell growth rates. Neoplasias and hyperplasias include "tumors," which may be either benign, premalignant or malignant.

The term "non-direct interaction" refers to any interactions that are not ionic nor covalent, such as hydrogen bonding or van der Waals interactions.

The term "optionally substituted" can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted as a substituent can themselves be substituted, if appropriate.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

A "peptide" is a sequence of at least two amino acids. Peptides can consist of short as well as long amino acid sequences, including proteins.

The terms "polycyclic group" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "protein" refers to series of amino acid residues connected one to the other by peptide bonds between the alpha-amino and carboxy groups of adjacent residues. In general, the term "protein" is used to designate a series of greater than 50 amino acid residues connected one to the other.

The language "reduced toxicity" is intended to include a reduction in any undesired side effect elicited by a compound when administered in vivo.

The term "sarcoma" is art recognized and refers to malignant tumors of mesenchymal derivation.

The term "subject" refers to animals such as mammals, including, but not limited to, primates (e.g., humans), cows, sheep, goats, horses, dogs, cats, rabbits, rats, mice and the like. In certain embodiments, the subject is a human.

The term "sulfhydryl" or "thiol" means —SH.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

The term "test compound" or "drug candidate" or "modulator" or grammatical equivalents as used herein describes any molecule, e.g., protein, oligopeptide, small organic molecule, polysaccharide, polynucleotide, etc., to be tested for the capacity to directly or indirectly modulate the activity of Tdp1.

The term "therapeutically effective amount" refers to that amount of the compound being administered sufficient to prevent development of or alleviate to some extent one or more of the symptoms of the condition or disorder being treated.

The terms "treating" and "treatment" refer to a method of alleviating or abating a disease and/or its attendant symptoms.

The term "tumor suppressor gene" refers to a gene that acts to suppress the uncontrolled growth of a cancer, such as a tumor.

As used herein, the terms "tyrosine-DNA phosphodiesterase" and "TDP" refer to a protein that is encoded by a tyrosine-DNA phosphodiesterase gene sequence or to a protein. In addition, the terms refer to enzymes that cleave the phosphodiester bond linking the active site tyrosine residue of topoisomerase I with 3'-terminus of DNA in topo I-DNA complexes.

Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Treatment of Diseases

In certain aspects, the invention provides a method of inhibiting Tdp1 activity in a subject, the method comprising administering to the subject a tetracycline compound capable of modulating the activity of Tdp1.

In one embodiment, the invention provides a method of inhibiting Tdp1 activity, wherein the tetracycline compound is a compound of formula I or formula Ia:

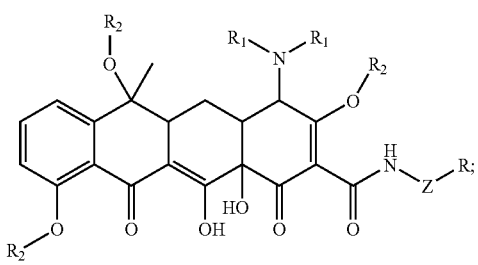

I

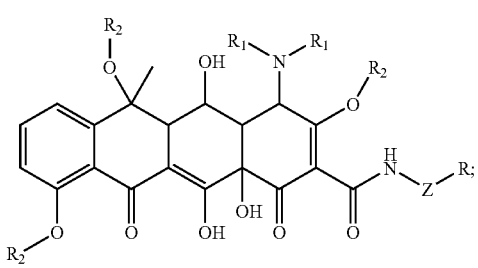

Ia wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In certain preferred aspects of the invention, such compounds of formula I or Ia are provided wherein R of formula I or Ia is not H when Z of formula I or Ia is absent.

In certain embodiments, the compound is a compound of Formula I. In certain embodiments, the compound is a compound of Formula Ia.

In certain embodiments, Z is absent. In other embodiments, R is H. In still other embodiments, Z is (C(R$^a$)(R$^b$))$_m$. In a further embodiment, Z is CH$_2$. In other embodiments, R is —NR$^a$R$^a$. In a further embodiment, Z is CH$_2$ and R is —NR$^a$R$^a$. In certain embodiments, each R$^a$ is independently H, alkyl, cycloalkyl, heterocycloalkyl, aralkyl, heteroaralkyl, aryl, heteroaryl, haloalkyl, or hydroxylalkyl, each of which may be optionally substituted; or two or more R$^a$ groups together with a heteroatom form a heterocyclic ring, which may be optionally substituted.

In other aspects, the invention provides a method of inhibiting Tdp1 activity in a subject identified as being in need of such treatment, the method comprising administering to the subject a tetracycline compound, wherein the tetracycline compound is capable of binding to Tdp1.

In another aspect, the invention provides a method of treating a Tdp1-related disorder in a subject, comprising administering to said subject in need thereof, an effective amount of a compound of formula I or Ia, such that said subject is treated for said disorder;

wherein the disorder is cancer, tumor, neoplasm, neovascularization, vascularization, cardiovascular disease, intravasation, extravasation, metastasis, arthritis, infection, Alzheimer's Disease, blood clot, atherosclerosis, melanoma, skin disorder, rheumatoid arthritis, diabetic retinopathy, macular edema, or macular degeneration, inflammatory and arthritic disease, or osteosarcoma.

In one aspect, the invention provides a method of treating cancer in a subject identified as in need of such treatment, the method comprising administering to said subject an effective amount of a compound of Formula I or Formula Ia:

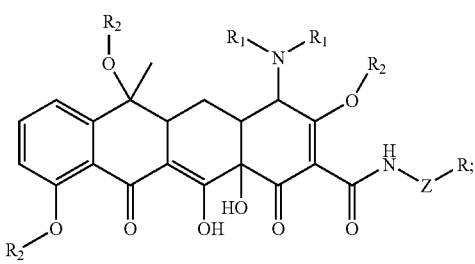

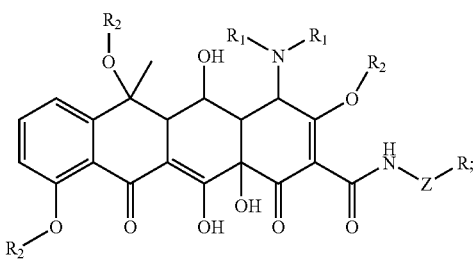

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$)) S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In a certain preferred aspects of the invention, such compounds of formula I or Ia are provided wherein R of formula I or Ia is not H when Z of formula I or Ia is absent.

In certain embodiments, the compound is a compound of Formula I. In certain embodiments, the compound is a compound of Formula Ia.

In certain embodiments, Z is absent. In other embodiments, R is H. In still other embodiments, Z is (C(R$^a$)(R$^b$))$_m$. In a further embodiment, Z is CH$_2$. In other embodiments, R is —NR$^a$R$^a$. In a further embodiment, Z is CH$_2$ and R is —NR$^a$R$^a$. In certain embodiments, each R$^a$ is independently H, alkyl, cycloalkyl, heterocycloalkyl, aralkyl, heteroaralkyl, aryl, heteroaryl, haloalkyl, or hydroxylalkyl, each of which may be optionally substituted; or two or more R$^a$ groups together with a heteroatom form a heterocyclic ring, which may be optionally substituted.

In certain embodiments, the compound is a Tdp1 inhibitor. In other embodiments, the compound of Formula I is:

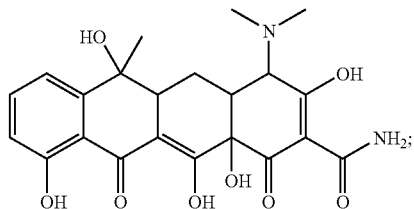

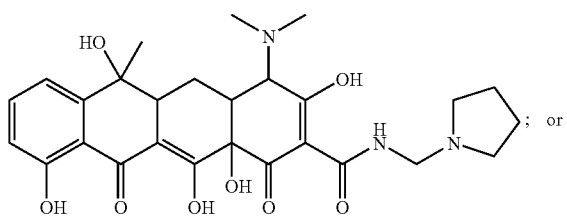

; or

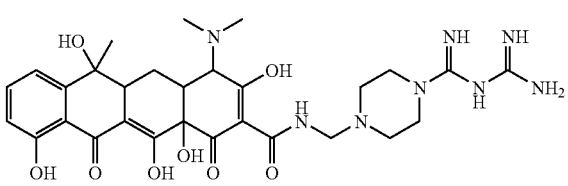

or a pharmaceutically acceptable salt thereof.

In certain embodiments, the compound of formula I or Ia is

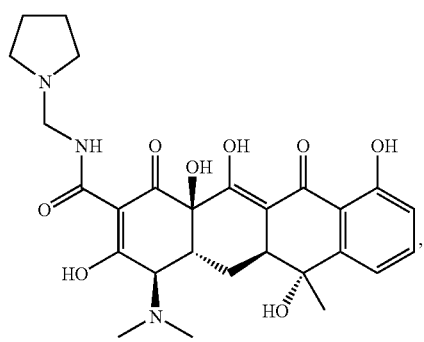

-continued

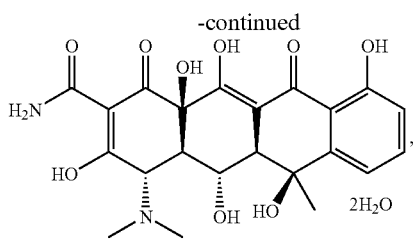

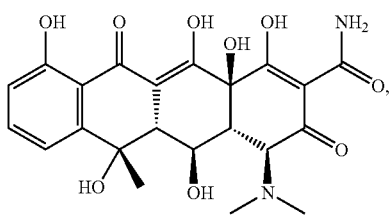, or

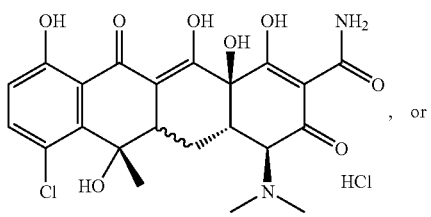, or

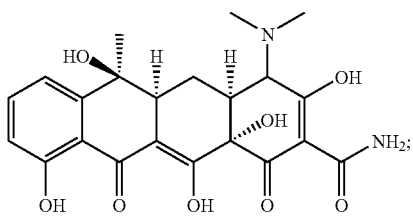

or a pharmaceutically acceptable salt thereof.

In other embodiments, the invention further comprising an additional therapeutic agent. In a further embodiment, the additional therapeutic agent is an anticancer compound.

In another embodiment, the step of administering the compound comprises administering the compound orally, topically, parentally, intravenously or intramuscularly.

In still another embodiment, the invention provides administering an effective amount of a composition comprising a tetracycline compound and a pharmaceutically suitable excipient.

In certain embodiments, the subject is a human.

In other embodiments, the step of administering the tetracycline compound comprises administering the compound in a dosage of between about 0.01 µg/kg/day and 100 mg/kg/day.

In yet other embodiments, the binding interaction is ionic, covalent, or a non-direct interaction.

In other aspects, the invention provides for the use of a tetracycline compound in the manufacture of a medicament for inhibiting or reducing cancer in a patient, the compound being of formula I or formula Ia:

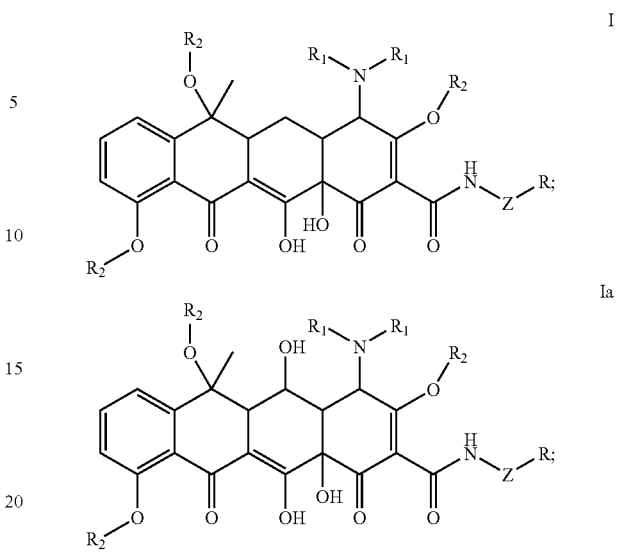

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2. In certain preferred aspects of the invention, such compounds of formula I or Ia are provided wherein R of formula I or Ia is not H when Z of formula I or Ia is absent.

In certain embodiments, the compound is a compound of Formula I. In certain embodiments, the compound is a compound of Formula Ia.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the present invention include all solid tumors, i.e., carcinomas and sarcomas, including Kaposi's sarcoma. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcoma, including Kaposi's sarcoma broadly include tumors whose cells are embedded in a fibrillar or homogeneous substance like embryonic connective tissue.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with MMP expression, particularly gelatinase expression, are especially susceptible to being inhibited or even induced to regress by means of the invention.

Thus, the treatable cancers include, for example, colon cancer, bladder cancer, breast cancer, melanoma, ovarian carcinoma, prostatic carcinoma, or lung cancer, and a variety of other cancers as well. The invention is especially useful in the inhibition of cancer growth in adenocarcinomas, including, for example, those of the prostate, breast, kidney, ovary, testes, and colon. The invention is further useful against melanomas, which derive from the melanocytic system in the skin and other organs.

A solid tumor can be malignant, e.g. tending to metastasize and being life threatening, or benign. Examples of solid tumors that can be treated according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated with a method of the present invention include arteriovenous (AV) malformations, particularly in intracranial sites and myoleomas. A method of the present invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperprobiferative disorders is also contemplated.

In certain embodiments, the present invention is directed to a method for inhibiting cancer growth, including processes of cellular proliferation, invasiveness, and metastasis in biological systems. The method includes the use of a tetracycline compound as an inhibitor of cancer growth. Preferably, the method is employed to inhibit or reduce cancer cell proliferation, invasiveness, metastasis, or tumor incidence in living animals, such as mammals.

The invention includes a method of inducing cytotoxicity (cell killing) in cancer cells or reducing the viability of cancer cells. For example, the invention can be used to induce cytotoxicity in cells of carcinomas of the prostate, breast, ovary, testis, lung, colon, or breast. The selective killing of the cancer cells can occur through apoptosis, necrosis, another mechanism, or a combination of mechanisms.

The killing of cancer cells can occur with less cytotoxicity to normal cells or tissues than is found with conventional cytotoxic therapeutics, preferably without substantial cytotoxicity to normal cells or tissues. For example, a tetracycline, e.g., CMT-3, can induce cytotoxicity in cancer cells while producing little or substantially no cytotoxicity in normal cells. Thus, unlike conventional cytotoxic anticancer therapeutics, which typically kill all growing cells, CMT-3 can produce differential cytotoxicity: tumor cells are selectively killed whereas normal cells are spared. Thus, in another embodiment, the invention is a method for inducing differential cytotoxicity in cancer cells relative to normal cells or tissue. This differential in cytotoxicity associated with the tetracycline compounds occurs as a result of apoptosis, necrosis, another mechanism, or a combination of such mechanisms.

The tetracycline compounds exhibit their cancer treatment properties at concentrations that lead to fewer side effects than those of known chemotherapeutic agents, and in some cases are substantially free of side effects. The tetracycline compounds are useful for extended treatment protocols, where other compounds would exhibit undesirable side-effects. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. The compounds are maximally effective if they can be delivered to the site of the tumor and are able to enter the tumor cells.

In the treatment of certain localized cancers, the degree of hydrophilicity of the tetracycline compound can be of lesser importance. Such compounds as tetracyclinonitrile (CMT-2), which has low solubility in aqueous systems, can be used in direct or topical treatment of skin cancers, e.g., melanoma or basal cell carcinoma, or by implantation into the brain to topically treat brain cancer.

The tetracycline compounds are effective to inhibit the proliferation, invasiveness, or metastasis of cancer cells in vitro, as well as in vivo. These compounds possess an excellent balance of properties, in that they are shown to possess unusually strong activity in inhibiting the cancer growth, including proliferation, invasiveness, or metastasis of cancer cells. Another advantage is that it has an unexpectedly long serum half-life (approximately 28 hr). Therefore, certain tetracyclines may only require periodic administration, e.g., once or twice per week.

In another embodiment, the method of the invention is effective to inhibit the enzymatic activity of matrix metalloproteinases, such as collagenases and gelatinases, associated with cancerous tumors in mammals. The gelatinolytic activity capable of inhibition may derive from gelatinase expression by the cancerous tumor or from normal, i.e., non-cancerous, tissue. In particular, the gelatinase activity may be derived from such normal tissues as epithelial tissue or stromal tissue. More preferably, the method can be used to inhibit excessive gelatinolytic activity associated with such tumors. This inhibition of observed gelatinolytic activity may be due to inhibition of MMP activity, down-regulation of MMP expression, or some other interference with the physiology associated with these gelatinases, such as inhibition of activation of the precursor form of the enzyme, pro-gelatinase (or pro-MMP).

The inhibition of cancer cells may result from inhibition of MMP activity, down-regulation of MMP expression, some other mechanism, or a combination of mechanisms. It is believed that all solid cancer types that express MMPs or that exhibit invasive or metastatic properties can be treated by the method of the invention. In some cases, the incidence or development of tumor foci can be inhibited or substantially prevented from occurring. Therefore, the method can be used as a prophylactic treatment, e.g., by administering the tetracycline compound to a mammal after detection of a gene product or metabolite associated with predisposition to a cancer but before any specific cancerous lesion is detected. Alternatively, the tetracycline compounds are useful for preventing cancer recurrence, for example, to treat residual cancer following surgical resection or radiation therapy.

The effect occurs over a wide range of concentrations, including at concentrations that are extraordinarily low. The amount of the tetracycline compound used according to the invention is an amount that is effectively inhibitory of cancer growth. An amount of a tetracycline compound is effectively inhibitory to cancer growth if it significantly reduces cellular proliferation or the potential of invasiveness or metastasis. Proliferation refers to the capacity of a tumor to increase its volume through cell division, typically measured as the "doubling rate." The inhibition of cellular proliferation by the present method means that the rate of growth is decreased. In some cases, the method can actually induce regression or diminution of tumor mass, if the rate of replenishment of the tumor cells through cell division is exceeded by the rate of cell death. Invasiveness refers to the potential of a tumor or tumor cells to invade other tissues, typically by breaking down the extracellular matrix of those tissues. Metastasis refers to the potential of a tumor or tumor cells to establish new tumor foci at sites distant from the primary site where the tumor began. Typically, metastasis proceeds by individual cells or groups of cells breaking off from the primary tumor and migrating, e.g., through the blood or lymph, to establish a new tumor focus in another tissue or organ. One locus common in tumor metastasis is in the lung, where the very fine vasculature of the lung tissue can often catch circulating tumor cells, permitting the establishment of a tumor focus therein. Some types of tumors metastasize to specific types of tissues.

The cancers treatable by means of the present invention occur in mammals. Mammals include, for example, humans, as well as pet animals such as dogs and cats, laboratory animals such as rats and mice, and farm animals such as horses and cows.

Human cancers are characterized by genomic instability, which leads to the accumulation of DNA lesions. Hence, tumor cells are highly dependent on normal repair for survival.

DNA topoisomerase I (Top1) is ubiquitous and essential in higher eukaryotes. It relieves DNA torsional stress and relaxes DNA supercoiling by introducing DNA single-strand breaks. Top1 can be trapped by DNA lesions that accumulate in cancer cells. Top1 is also the target of the anticancer agent camptothecin and non-camptothecin inhibitors. Top1 inhibitors damage DNA by trapping covalent complexes between the Top1 catalytic tyrosine and the 3'-end of the broken DNA. Tyrosyl-DNA phosphodiesterase (Tdp1) repairs Top1-DNA covalent complexes by hydrolyzing the tyrosyl-DNA bond.

Tdp1 inhibitors are therefore useful as anticancer agents both in monotherapy and in combination with other anticancer compounds (particularly DNA-targeted anticancer compounds) such as Top1 inhibitors. Tumor cells, whose repair pathways are commonly deficient, might be selectively sensitized to Top1 inhibitors compared to normal cells that contain redundant repair pathways. Moreover, Tdp1 inhibitors might also be effective by themselves as anticancer agents as oncogenic activation tends to increase free radical production and genomic instability (Cerutti Pa. (1985) *Science* 227 (4685):375-381; Kc S et al. *Mutat Res.* (2006) 29 593(1-2): 64-79.; Vafa et al., *Mol Cell* 9(5):1031-1044 (2002)).

Thus, in certain embodiments, the invention provides methods for treating cancer and other cell proliferative disorders by administering to a subject in need thereof an effective amount of a combination of a Tdp1 inhibitor of this invention together with a TopI inhibitor. A variety of TopI inhibitors have been reported, including camptothecin, irinotecan, topotecan, saintopin, and derivatives and analogs thereof. In another aspect, the invention provides pharmaceutical compositions including a Tdp1 inhibitor of this invention together with a Top1 inhibitor, optionally including a pharmaceutically-acceptable carrier or excipient.

In another aspect, the invention provides methods and compositions for the treatment or prevention of parasitic disease. Tdp1 inhibitors may be valuable as anti-infectious agents since the gene is present in parasites, including *Trypanosoma brucei rhodesiense, Trypanosoma brucei gambiense*, and *Plasmodium* spp. including *P. vivax, P. falciparum, P. ovale*, and *P. malaria*. Thus, in one aspect, the invention provides methods for treating or preventing a parasitic infection caused by a parasite expressing Tbp1, the method including the step of administering to a subject in need thereof an effective amount of a Tdp1 inhibitor according to this invention. In another aspect, the invention provides pharmaceutical compositions for treatment or preention of parasitic disease, including a Tdp1 inhibitor of this invention together pharmaceutically-acceptable carrier or excipient.

Tetracycline compounds used to treat cancer and other Tdp1-related disorders include the following compounds, or a pharmaceutically acceptable salt thereof:

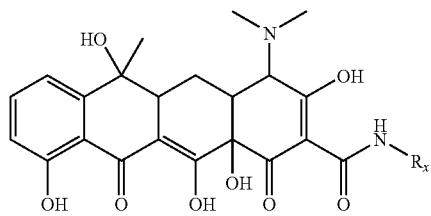

wherein Rx is selected from the following:

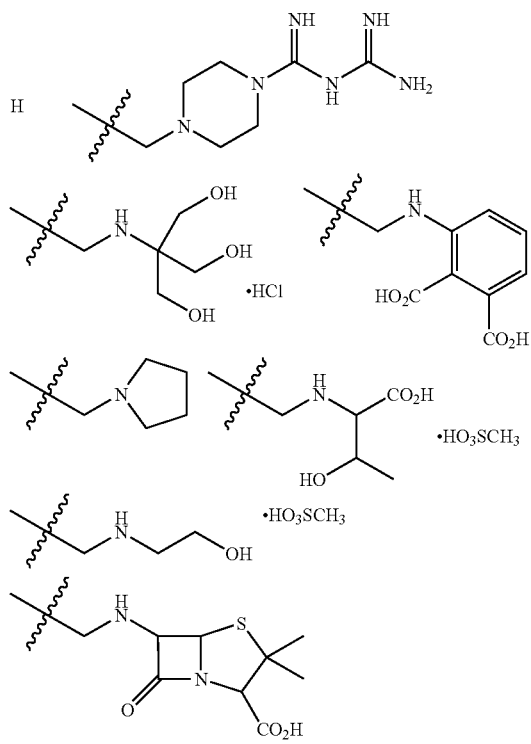

Compounds of the Invention

In one aspect, the invention provides a tetracycline compound of formula I or Ia:

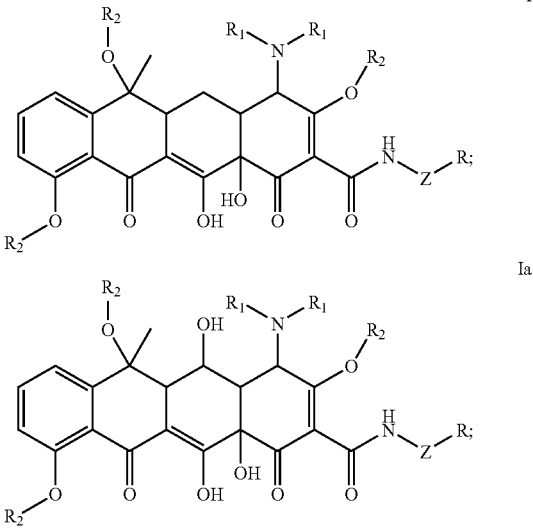

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and
each p is independently 0, 1, or 2.

In certain preferred aspects of the invention, a tetracycline compound of the above formula I or Ia is provided wherein R of formula I or Ia is not H when Z of formula I or Ia is absent.

In certain embodiments, the compound is a compound of Formula I. In certain embodiments, the compound is a compound of Formula Ia.

Formulation, Administration, Kits, and Pharmaceutical Compositions

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

In certain aspects, the invention provides for a pharmaceutical composition comprising a compound of Formula I or Formula Ia:

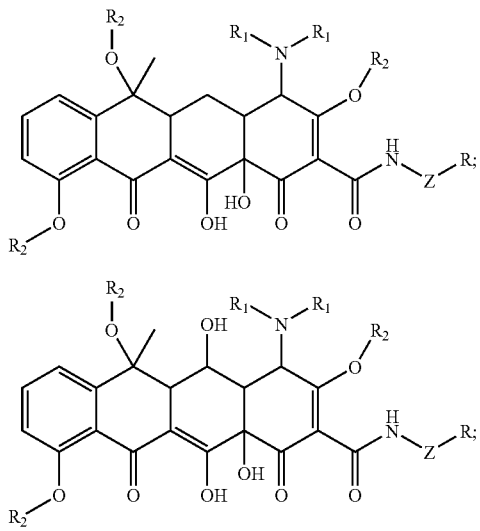

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$^m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each R$^a$ is independently, H, alkyl, alkenyl, alkynyl, cycloalkyl, heterocycloalkyl, aralkyl, heteroaralkyl, aryl, heteroaryl, haloalkyl, —OR$^b$, —SR$^b$, —NR$^b$R$^b$, hydroxylalkyl, alkylcarbonylalkyl, mercaptoalkyl, aminoalkyl, sulfonylalkyl, sulfonylaryl, or thioalkoxy; each of which may be optionally substituted; and wherein two or more R$^a$ groups, when attached to a heteroatom, may together form a heterocyclic ring with said heteroatom, wherein the heterocyclic ring may be optionally substituted;

each R$^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and
each p is independently 0, 1, or 2;

together with a pharmaceutically-acceptable carrier or excipient.

In certain preferred aspects of the invention, pharmaceutical compositions are provided comprising a tetracycline compound of the above Formula I or Ia wherein R of Formula I or Ia is not H when Z of Formula I or Ia is absent. In certain embodiments, the compound is a compound of Formula I. In certain embodiments, the compound is a compound of Formula Ia.

In another aspect, the invention provides for a kit comprising an effective amount of a tetracycline compound in unit dosage form, together with instructions for administering the tetracycline compound to a subject suffering from cancer, wherein the compound is of formula I or formula Ia:

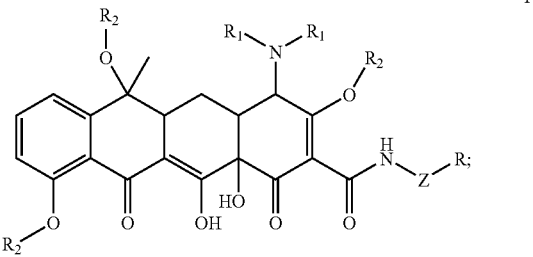

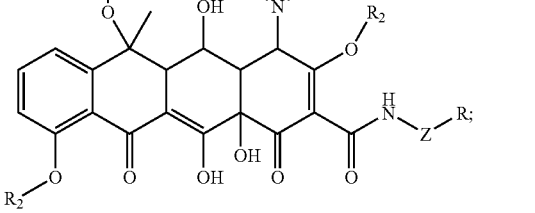

wherein,

Z is S(O), S(O)$_2$, N(R$^b$), C(O), C(S), C(S)NR$^b$, C(NR), C(NR)NR$^b$, C(O)NR$^b$, C(O)O, (C(R$^a$)(R$^b$))$_m$, (C(R$^a$)(R$^b$))$_m$NR$^b$, (C(R$^a$)(R$^b$))$_m$O, (C(R$^a$)(R$^b$))$_m$S(O)$_p$, NR$^b$C(O)NR$^b$, NR$^b$C(S)NR$^b$, NR$^b$C(O), NR$^b$C(O)O, NR$^b$C(NR)NR$^b$, NR$^b$C(S)O, NR$^b$S(O)$_p$NR$^b$, C(NR)O, S(O)$_p$NR$^b$, or absent;

each R$_1$ and R$_2$ is independently H, alkyl, cycloalkyl, heterocycloalkyl, aryl, heteroaryl, aralkyl, heteroaralkyl, hydroxylalkyl, —C(O)R$^a$, —C(S)R$^a$, —C(NR)R$^a$, haloalkyl, —S(O)R$^a$, —S(O)$_2$R$^a$, —P(O)R$^a$R$^a$, —P(S)R$^a$R$^a$, or alkylcarbonylalkyl; each of which may be optionally substituted;

R is H, alkyl, alkylcarbonyl, —OR$^b$, —SR$^b$, —NR$^a$R$^a$, hydroxylalkyl, —C(O)R$^a$, —OC(O)R$^a$, —SC(O)R$^a$, —NR$^b$C(O)R$^a$, —C(S)R$^a$, —OC(S)R$^a$, —SC(S)R$^a$, —NR$^b$C(S)R$^a$, —C(NR)R$^a$, —OC(NR)R$^a$, —SC(NR)R$^a$, —NR$^b$C(NR)R$^a$, —SO$_2$R$^a$, —S(O)R$^a$, —NR$^b$SO$_2$R$^a$, —OS(O)$_2$R$^a$, —OP(O)R$^a$R$^a$, —P(O)R$^a$R$^a$, halo, haloalkyl, aminoalkyl, mercaptoalkyl, cyano, nitro, nitroso, azide, alkylcarbonylalkyl, cycloalkyl, heterocyclyl, heterocycloalkyl, aryl, aralkyl, heteroaryl, heteroaralkyl, or isothionitro; each of which may be optionally substituted;

each $R^a$ is independently, H, alkyl, alkenyl, alkynyl, cycloalkyl, heterocycloalkyl, aralkyl, heteroaralkyl, aryl, heteroaryl, haloalkyl, —$OR^b$, —$SR^b$, —$NR^bR^b$, hydroxyalkyl, alkylcarbonylalkyl, mercaptoalkyl, aminoalkyl, sulfonylalkyl, sulfonylaryl, or thioalkoxy; each of which may be optionally substituted; and wherein two or more $R^a$ groups, when attached to a heteroatom, may together form a heterocyclic ring with said heteroatom, wherein the heterocyclic ring may be optionally substituted;

each $R^b$ is independently H, alkyl, alkenyl, alkynyl, cycloalkyl, heterocyclyl, heterocycloalkyl, aralkyl, heteroaralkyl, aryl, or heteroaryl; each of which may be optionally substituted;

each m is independently 1, 2, 3, 4, 5, 6, 7, or 8; and each p is independently 0, 1, or 2.

In certain preferred aspects of the invention, such kits are provided that comprise a compound of the above formula I or Ia wherein R of formula I or Ia is not H when Z of formula I or Ia is absent. In certain embodiments, the compound is a compound of Formula I. In certain embodiments, the compound is a compound of Formula Ia.

The phrase "pharmaceutically acceptable" refers to those compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, involved in carrying or transporting the subject chemical from one organ, or portion of the body, to another organ, or portion of the body. Each carrier must be "acceptable" in the sense of being compatible with the other ingredients of the formulation and not injurious to the patient.

A therapeutically effective amount can be administered in one or more doses. The term "administration" or "administering" includes routes of introducing the compound(s) to a subject to perform their intended function. Examples of routes of administration which can be used include injection (subcutaneous, intravenous, parenterally, intraperitoneally, intrathecal), oral, inhalation, rectal and transdermal.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

Methods of preparing these compositions include the step of bringing into association a compound(s) with the carrier and, optionally, one or more accessory ingredients. These compositions may also contain adjuvants such as preservatives, wetting agents, emulsifying agents and dispersing agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. Alternatively, delayed absorption of a parenterally-administered drug form is accomplished by dissolving or suspending the drug in an oil vehicle.

Regardless of the route of administration selected, the compound(s), which may be used in a suitable hydrated form, and/or the pharmaceutical compositions of the present invention, are formulated into pharmaceutically-acceptable dosage forms by conventional methods known to those of skill in the art.

In certain embodiments, the pharmaceutical compositions are suitable for topical, intravenous, intratumoral, parental, or oral administration. The methods of the invention further include administering to a subject a therapeutically effective amount of a conjugate in combination with another pharmaceutically active compound. Pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference.

Formulations are provided to a subject in an effective amount. The term "effective amount" includes an amount effective, at dosages and for periods of time necessary, to achieve the desired result. An effective amount of conjugate may vary according to factors such as the disease state, age, and weight of the subject, and the ability of the compound to elicit a desired response in the subject. Dosage regimens may be adjusted to provide the optimum therapeutic response.

The effective amount is generally determined by the physician on a case-by-case basis and is within the skill of one in the art. As a rule, the dosage for in vivo therapeutics or diagnostics will vary. Several factors are typically taken into account when determining an appropriate dosage. These factors include age, sex and weight of the patient, the condition being treated, and the severity of the condition.

Suitable dosages and formulations of immune modulators can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein. Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

In terms of treatment, an effective amount is an amount that is sufficient to palliate, ameliorate, stabilize, reverse or slow the progression of a cancerous disease or otherwise reduce the pathological consequences of the cancer. A therapeutically effective amount can be provided in one or a series of administrations. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the form of the compound being administered.

Ascertaining dosage ranges is well within the skill of one in the art. The dosage of conjugates can range from about 0.001 µg/kg/day to about 500 mg/kg/day. Methods for administering compositions are known in the art. Such dosages may vary, for example, depending on whether multiple administrations are given, tissue type and route of administration, the condition of the individual, the desired objective and other factors known to those of skill in the art. Administrations can be conducted infrequently, or on a regular weekly basis until a desired, measurable parameter is detected, such as diminution of disease symptoms. Administration can then be diminished, such as to a biweekly or monthly basis, as appropriate.

Such dosages may vary, for example, depending on whether multiple administrations are given, tissue type and route of administration, the condition of the individual, the desired objective and other factors known to those of skill in the art.

Following administration of the composition, it can be necessary to wait for the composition to reach an effective tissue concentration at the site of the disorder before detection. Duration of the waiting step varies, depending on factors such as route of administration, location, and speed of movement in the body. In addition, where the compositions are coupled to molecular carriers, the rate of uptake can vary, depending on the level of receptor expression on the surface of the cells. For example, where there is a high level of receptor expression, the rate of binding and uptake is increased. Determining a useful range of waiting step duration is within the level of ordinary skill in the art and may be optimized.

The tetracycline compounds useful according to the method of the invention appear to exhibit their beneficial effect in a dose-dependent manner. Thus, within broad limits, administration of larger quantities of a tetracycline compound has been observed to inhibit cancer cell growth or invasiveness to a greater degree than does administration of a smaller amount. Moreover, efficacy has been observed at dosages below the level at which toxicity is seen in normal cells or at the organismal level. Accordingly, one of the advantages of the invention is that the debilitating side effects usually attendant upon conventional cytotoxic cancer treatments are reduced, and preferably avoided.

Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, compositions are preferably supplied in unit dosage form suitable for administration of a precise amount. Also contemplated by this invention are slow-release or sustained release forms, whereby a relatively consistent level of the active compound are provided over an extended period.

Another method of administration is intravascular, for instance by direct injection into the blood vessel, or surrounding area. Further, it may be desirable to administer the compositions locally to the area in need of treatment; this can be achieved, for example, by local infusion during surgery, by injection, by means of a catheter, or by means of an implant, said implant being of a porous, non-porous, or gelatinous material, including membranes, such as silastic membranes, or fibers.

Although methods and materials similar or equivalent to those described herein can be used in the practice of the present invention, preferred methods and materials are described above. The materials, methods, and examples are illustrative only and not intended to be limiting. Other features and advantages of the invention will be apparent from the detailed description and from the claims.

Enteral administration is a preferred route of delivery of the tetracycline, and compositions including the tetracycline compound with appropriate diluents, carriers, and the like are readily formulated. Liquid or solid (e.g., tablets, gelatin capsules) formulations can be employed. It is among the advantages of the invention that, in many situations, the tetracycline compound can be delivered orally, as opposed to parenteral delivery (e.g., injection, infusion) which is typically required with conventional chemotherapeutic agents.

Parenteral use (e.g., intravenous, intramuscular, subcutaneous injection) is also contemplated, and formulations using conventional diluents, carriers, etc., such as are known in the art can be employed to deliver the compound.

Alternatively, delivery of the tetracycline compound can include topical application. Compositions deemed to be suited for such topical use include as gels, salves, lotions, ointments and the like. In the case of tumors having foci inside the body, e.g., brain tumors, the tetracycline compound can be delivered via a slow-release delivery vehicle, e.g., a polymeric material, surgically implanted at or near the lesion situs.

The maximal dosage for a subject is the highest dosage that does not cause undesirable or intolerable side effects. For the purpose of the present invention, side effects may include clinically significant antimicrobial or antibacterial activity, as well as toxic effects. The practitioner is guided by skill and knowledge in the field, and the present invention includes, without limitation, dosages that are effective to achieve the described phenomena.

The invention can also be practiced by including with the tetracycline compound one or more other anti-cancer chemotherapeutic agents, such as any conventional chemotherapeutic agent. The combination of the tetracycline compound with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radio-isotopes, as well as natural products. For example, the non-anti-microbial tetracycline compound can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinomas of the breast and prostate, in which the tumors can include gonadotropin-dependent and gonadotropin-independent cells, the tetracycline can be administered in conjunction with leuprolide or goserelin (synthetic peptide analogs of LH-RH). Other antineoplastic protocols include the use of a tetracycline compound with another treatment modality, e.g., surgery, radiation, other chemotherapeutic agent, etc., referred to herein as "adjunct antineoplastic modalities." Thus, the method of the invention can be employed with such conventional regimens with the benefit of reducing side effects and enhancing efficacy.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Another embodiment is a compound of any of the formulae herein made by a process delineated herein, including the processes exemplified in the schemes and examples herein. Another aspect of the invention is a compound of any of the formulae herein for use in the treatment or prevention in a subject of a disease, disorder or symptom thereof delineated herein. Another aspect of the invention is use of a compound of any of the formulae herein in the manufacture of a medicament for treatment or prevention in a subject of a disease, disorder or symptom thereof delineated herein.

EXAMPLES

Example 1

Gel-Based Assay

Preparation of Tdp1 substrates: HPLC purified oligonucleotides N14Y (Plo et al., (2003) *DNA Repair (Amst)* 2(10): 1087-1100) were labeled at their 5'-end with [γ-$^{32}$P]-ATP (Perkin-Elmer Life Science Co., Boston, Mass.) by incubation with 3'-phosphatase free T4 polynucleotide kinase (Roche applied Science, Indianapolis, Ind.) according to the manufacturer's protocols. Unincorporated nucleotides were removed by Sephadex G-25 spin-column chromatography (Mini Quick Spin Oligo Columns, Roche, Indianapolis, Ind.). For the production of the oligonucleotide duplexes D14Y, N14Y was mixed with the complementary oligonucleotide in equal molar ratios in annealing buffer (10 mM Tris-HCl pH 7.5, 100 mM NaCl, 10 mM $MgCl_2$), heated to 96° C., and allowed to cool down slowly (over 2 h) to room temperature.

Assay: Unless indicated otherwise, Tdp1 assays were performed in 20 μl mixtures containing 50 mM Tris-HCl, pH 8.0, 80 mM KCl, 2 mM EDTA, 1 mM dithiothreitol (DTT), and 40 μg/ml bovine serum albumin (BSA). For initial screening of Tdp1 inhibitors, 25 nM of 5'-$^{32}$P-labeled substrate (D14Y) was reacted with 1 ng Tdp1 (≈0.7 nM) in the absence or presence of inhibitor for 20 min at 25° C. Reactions were stopped by addition of 60 μl of gel loading buffer (98% (v/v) formamide, 1% (w/v) xylene cyanol, 1% (w/v) bromophenol blue). Twelve μl of aliquots were resolved in 20% denaturing polyacrylamide (AccuGel, National Diagnostics, Atlanta, Ga.) (19:1) gel containing 7 M urea. After drying, gels were exposed overnight to PhosphorImager screens (Molecular Dynamics, Sunnyvale, Calif.). Screens were scanned, and images were obtained with the Molecular Dynamics software (Sunnyvale, Calif.). Densitometry analyses were performed using ImageQuant 5.2 software package (Amersham Biosciences, Piscataway, N.J.). Tdp1 activity was determined by measuring the fraction of substrate converted into 3'-phosphate DNA product by densitometry analysis of the gel image (Debethune et al., 2002). Figures show representative results that were consistently reproduced at least three times.

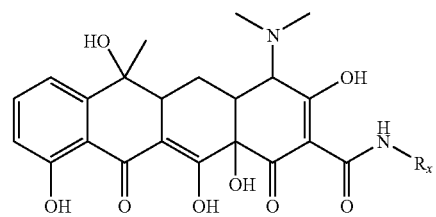

wherein Rx is selected from the following:

TABLE 1

| $R_x$ | IC50 (μM) |
|---|---|
| H | 785 |
| (piperazinyl-guanidine structure with NH, NH, $NH_2$) | 9 |
| (aminotriol structure with OH, OH, OH, ·HCl) | 29 |
| (aminobenzene dicarboxylic acid structure with $HO_2C$, $CO_2H$) | 49 |
| (pyrrolidinylmethyl structure) | 84 |
| (threonine-like structure with $CO_2H$, OH, ·$HO_3SCH_3$) | 106 |
| (aminoethanol structure with ·$HO_3SCH_3$, OH) | 122 |
| (β-lactam/penicillin-like structure with S, $CO_2H$) | 141 |

Tdp1 inhibitors have become a major area of drug research and structure-based design, with Tdp1, works synergistically and selectively in the cancer cells. Tdp1 can repair DNA topoisomerase I (Top1) covalent complexes by hydrolyzing the tyrosyl-DNA phosphodiester bond. The natural substrate of Tdp1 is large and complex, consisting of tyrosine or possibly a tyrosine-containing peptide moiety linked to a single strand of DNA via a 3' phosphodiester bond (Interthal, H.; Pouliot, J. J. *PNAS,* 98, 21 (2001)). In the present study, in order to determine how the inhibitors may be binding with the active site of Tdp1 N domain, we report docking the inhibitors into a structural model of Tdp1 enzyme, based on a multiple crystal structures of Tdp1 substrate complex with resolution 2.0 Å or better inhibitors to obtain information about their preferred conformations and their potential binding interactions with the Tdp1 and Top1 N-terminal domain.

Materials and Methods

Computational modeling was performed using Glide software (Schrodinger Inc.) on a Silicon Graphics workstation. All minimizations and docking were performed with the OPLS2003 force field. The dimmer complex with peptide [1NOP (Davies D. R., Champoux J. J., *J. Med. Chem.,* 324, 917-932, 2002), 1RFF (Davies, D. R. et al., *Chem. & Biol.* 10, 139 (2003))] and with octopamine (1RHO) (Davies, D. R. et al., *J. Med. Chem.* 47, 829 (2004)) were used. Chain A from the crystal structure of Top 1 and Tdp1 bound to the NT domain was used as the starting geometry for the modeling study. The model was built from an x-ray crystal structure of the complexes: 1NOP, 1RFF, 1RHO using the Maestro 7.5.

Example 2

Eight crystal structures (shown in Table 1, Davies, D. R. et al., *J. Med. Chem.* 47, 829 (2004)) of Tdp1 with vanadate, oligonucleotides and peptides or peptide analogues were determined. Those eight complex include peptides of varying length and sequence, non-peptide analogues of tyrosine and oligonucleotides of varying length of sequence. The conformations of the 8WT (Top 1-peptide) and eight other crystallographic peptides in vanadate complex with Tdp1 are significantly different from the conformation of the corresponding residues in the crystal structures of Top 1 bound to DNA (1NOP) (Davies, D. R., et al., *Structure* 10 237 (2002))

Example 3

Two compounds were used, as shown below by structures (a) and (b):

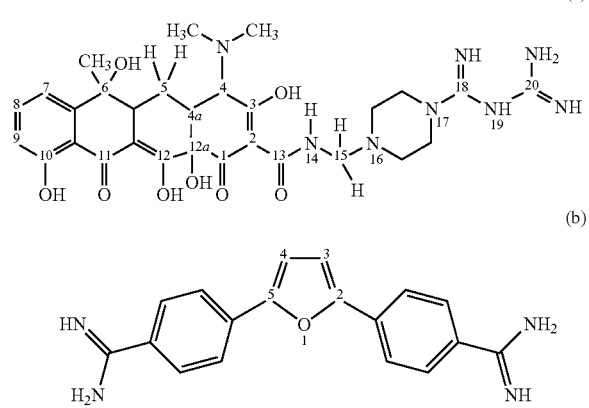

The data for the two compounds is as follows:
(a) $IC_{50}$ ss14Y=12 μM; $IC_{50}$ ds14Y=19 μM; MW=626.66
(b) $IC_{50}$ ss14Y=45 μM; $IC_{50}$ ds14Y=13.2 μM; MW=304.35

The two dimensional structures of Compounds (a) and (b) were minimized before analyzing the interactions between the ligand and the receptor. The compounds were optimized using the OPLS2003 force field, using a PRCG to convergence and a distance dependent dielectric constant of 1 for the electrostatic treatment. Minimization was done using conjugate gradient minimization. Maximum number of cycles was set to 1000, gradient criteria: 0.001. The complex was modeled in the N-terminal domain. The ligand compounds were docked by standard precision (SP) and with option: dock flexibly, which allow flips of 5 and 6 member rings. The best poses of compounds were finally selected based on the docking score, Emodel and the interactions made by the compounds with the active site of Tdp1.

Figure 1B:
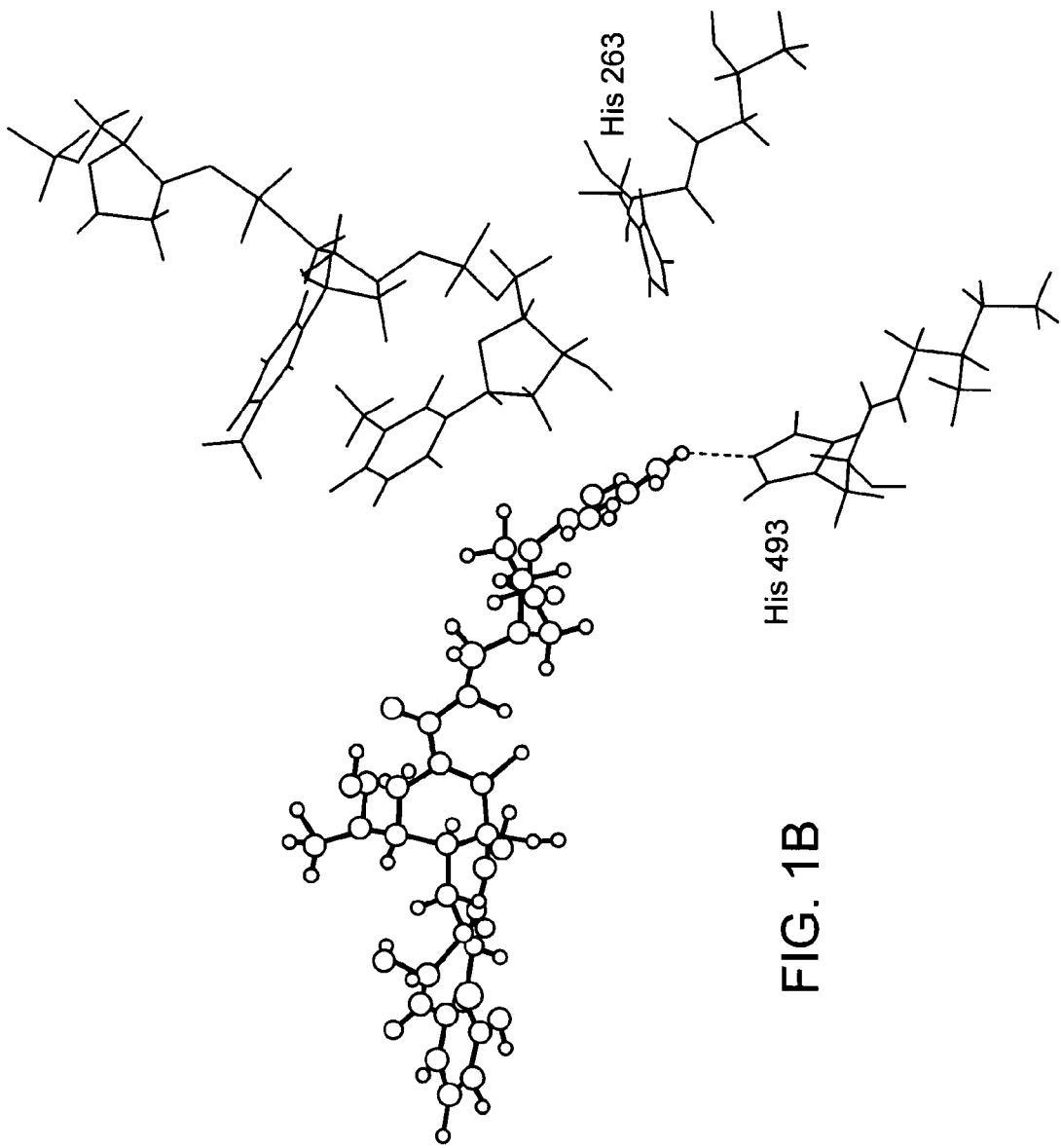
Figure 1C:
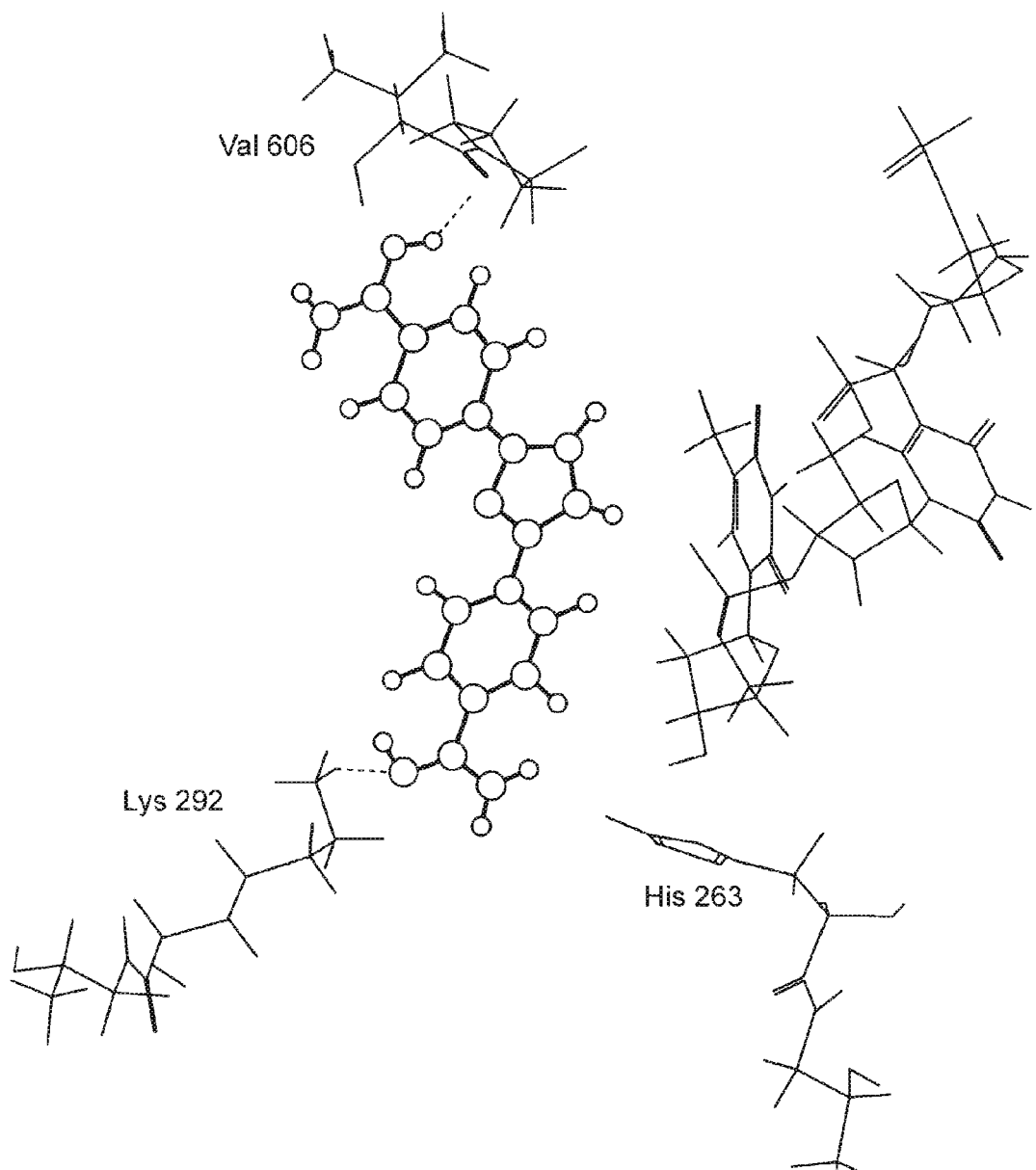
Figure 1D:
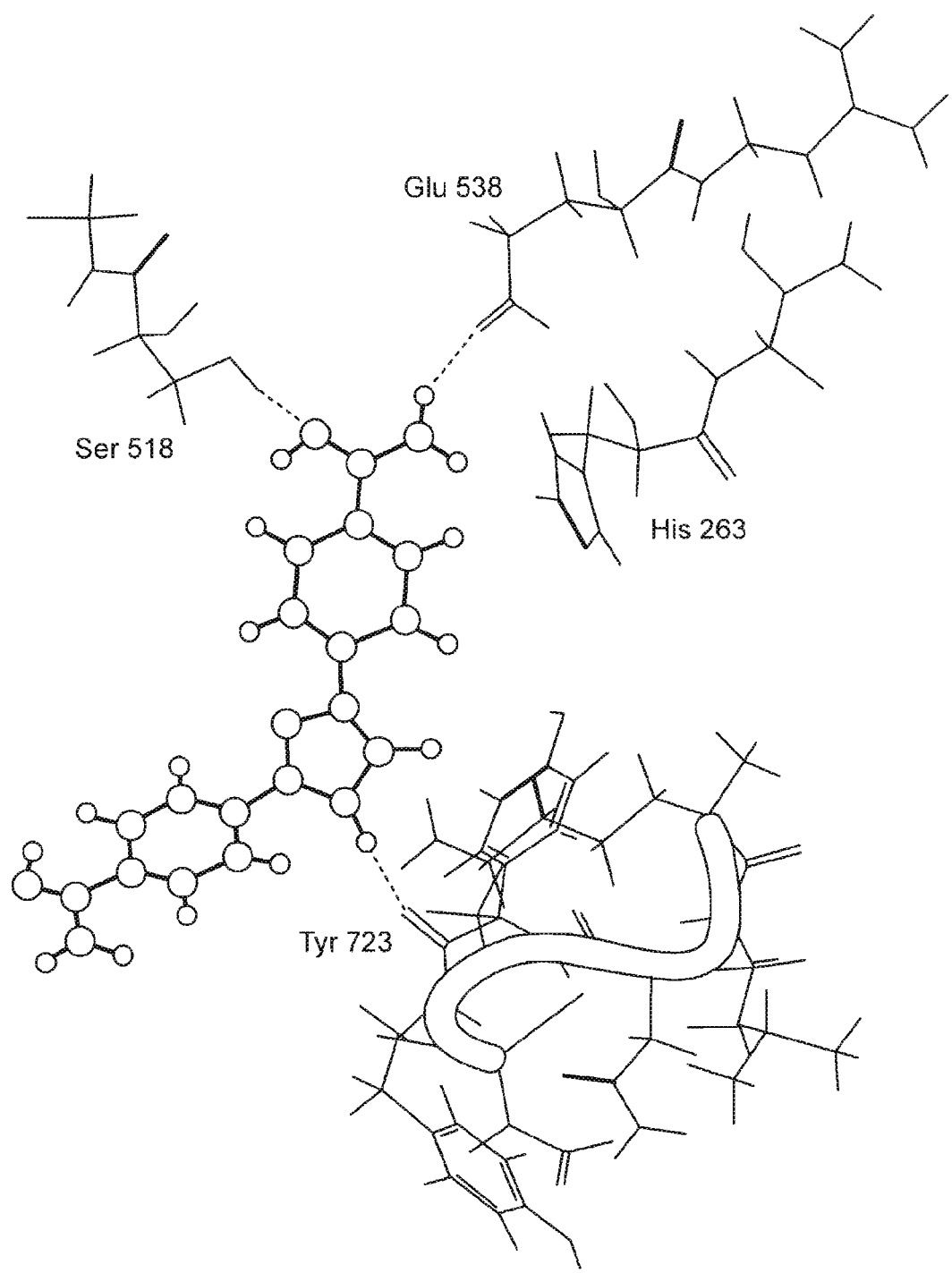
Figure 2A:
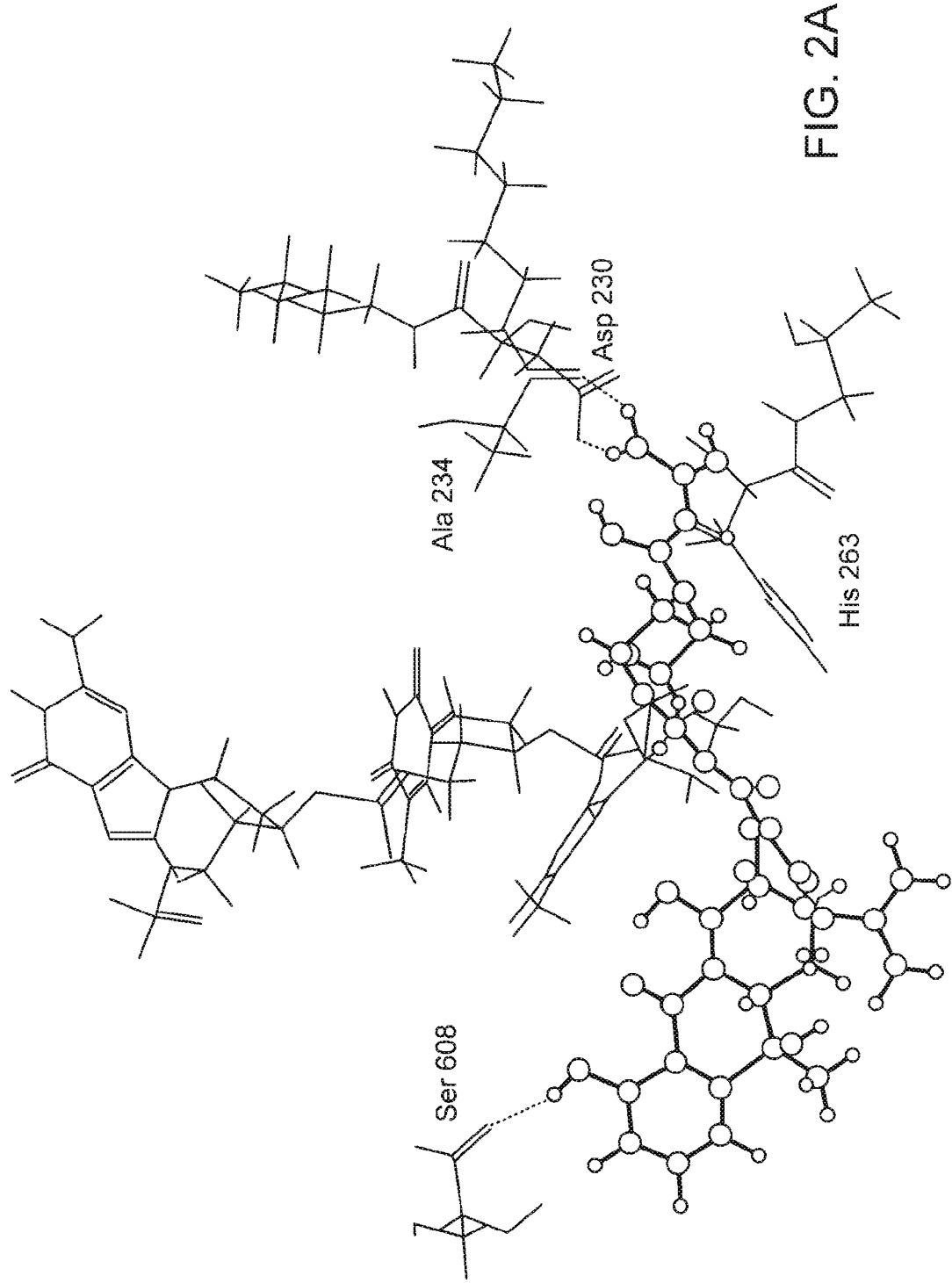
FIG. 2 shows Compounds (a) and (b) (1NOP) (shown in ball-and stick) docked in the binding site of the Tdp1 N domain. Hydrogen bonds are represented as dashed orange lines and contacts as dashed green lines. For clarity, only important residues and atoms are shown. Color codes used: nitrogen—blue, oxygen—red, carbon—black, hydrogen—grey, protein—blue tube, His 263—red.
Figure 2B:
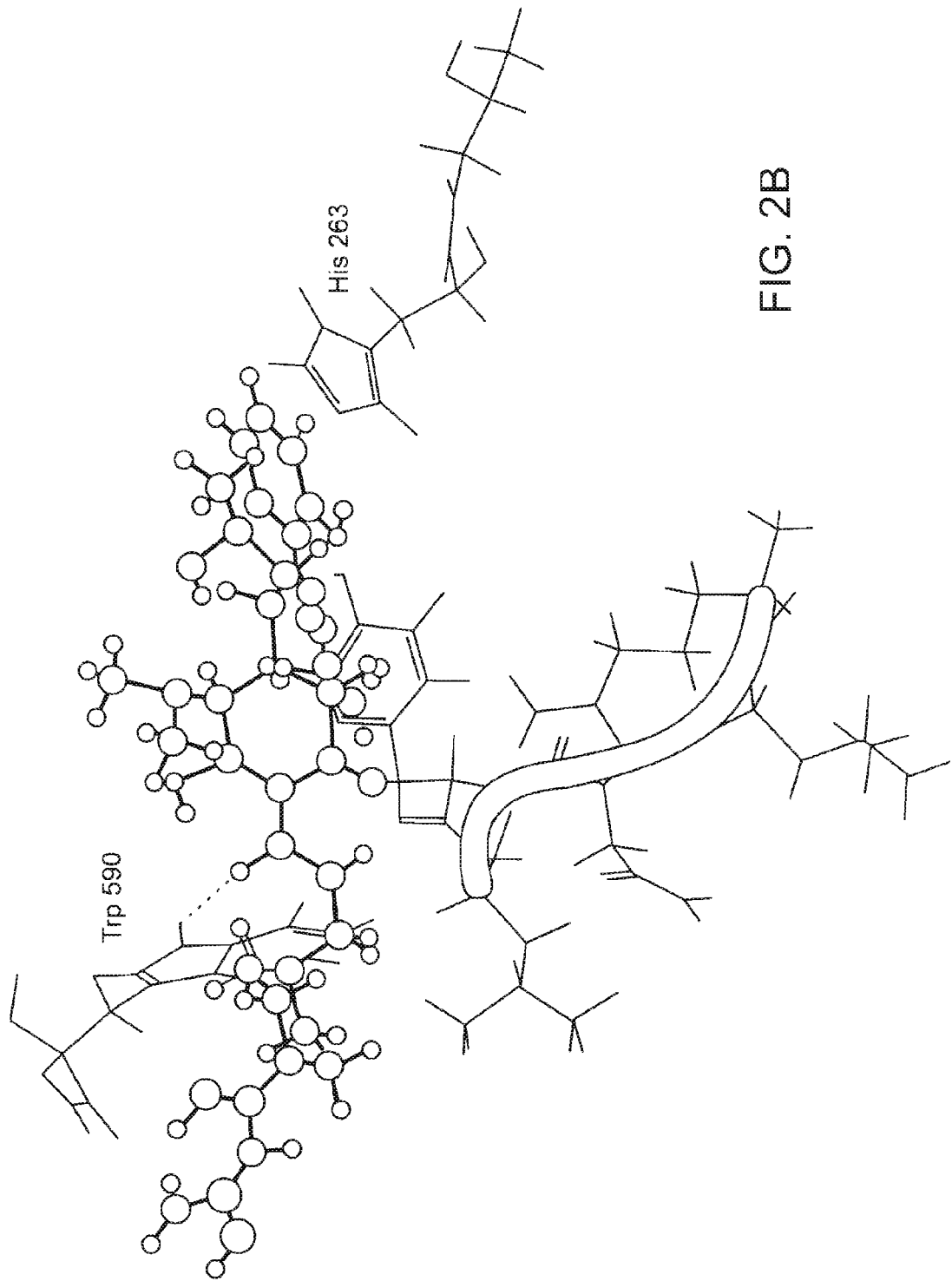
Figure 2C:
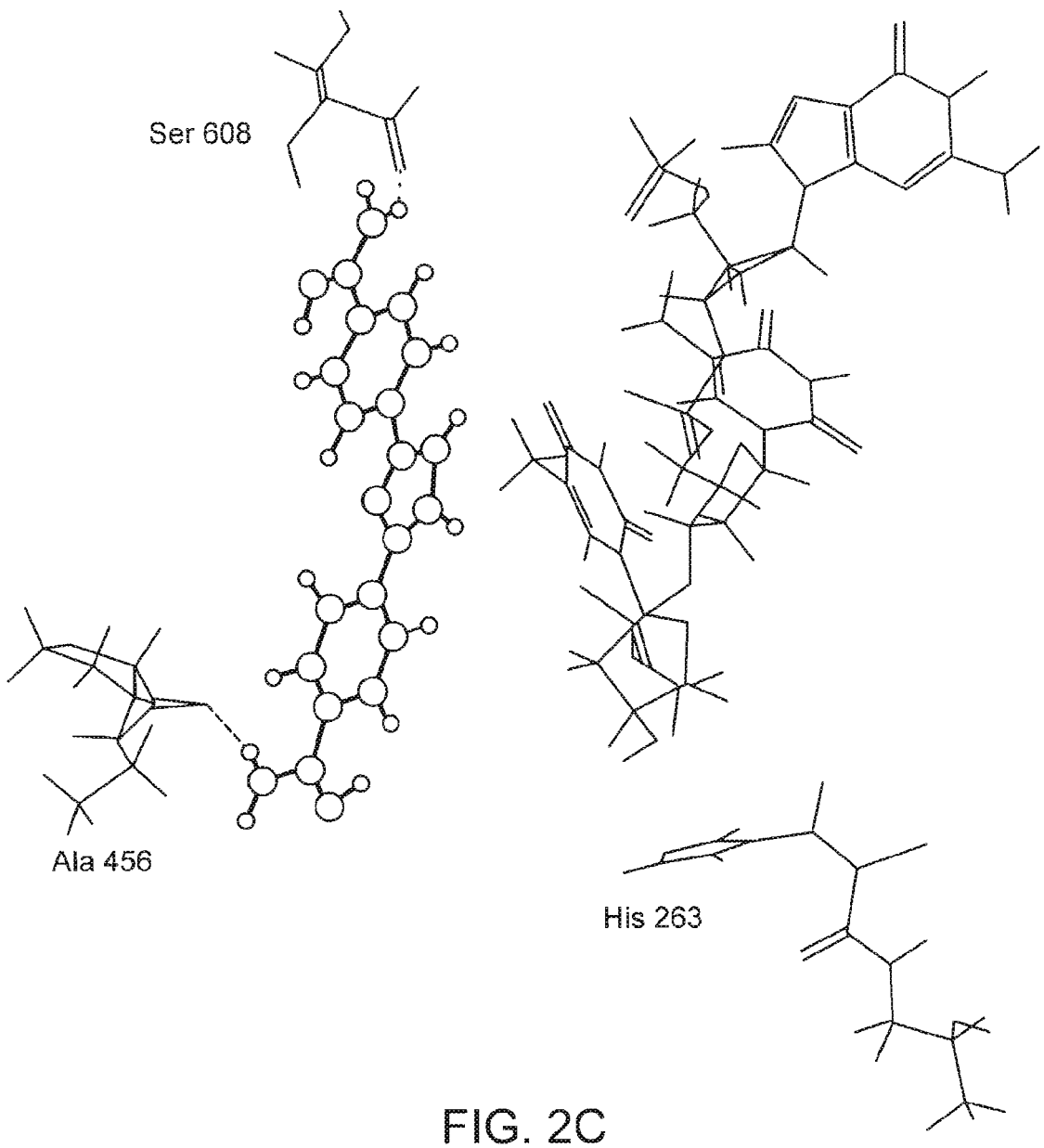
Figure 2D:
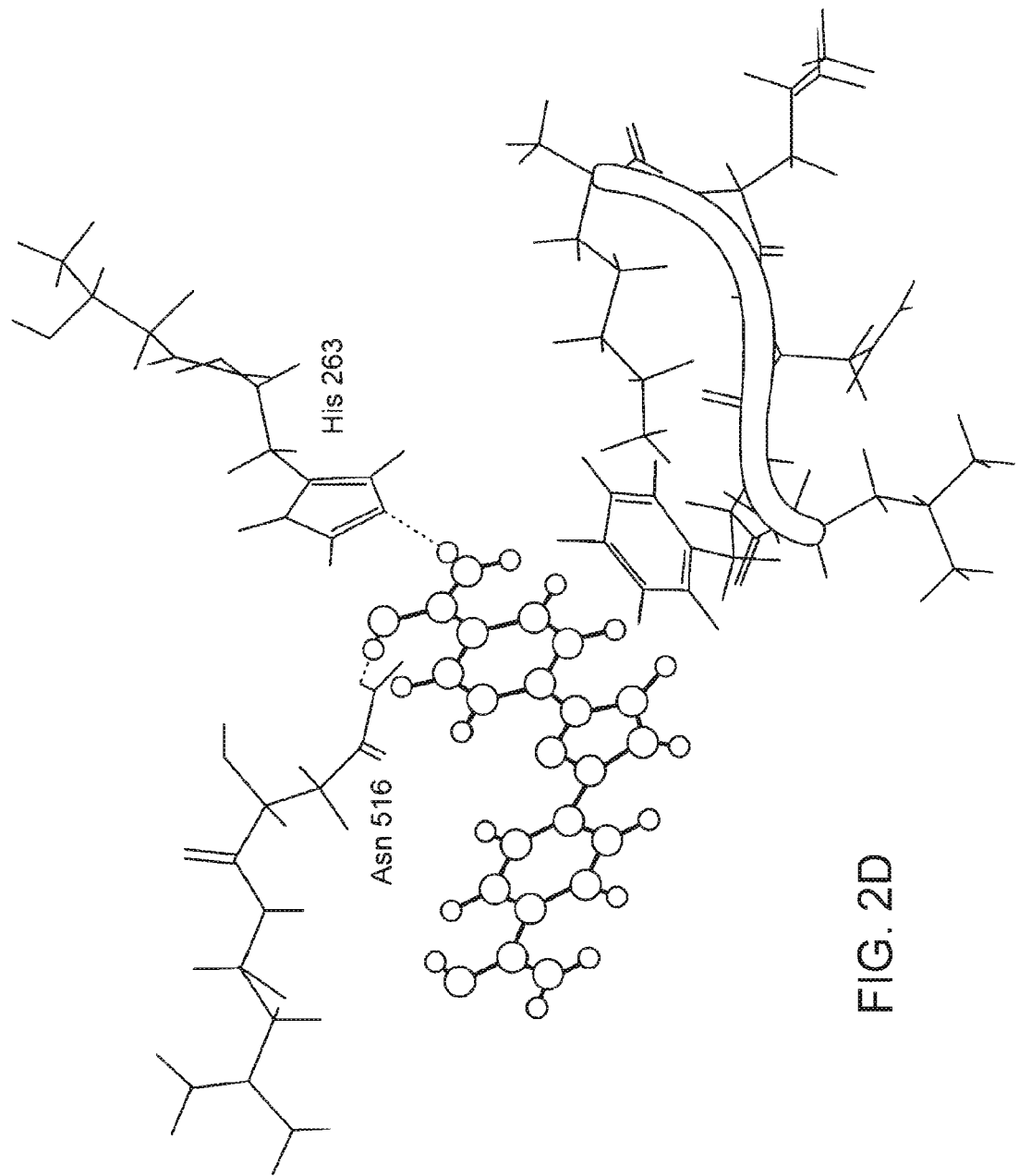
Figure 3A:
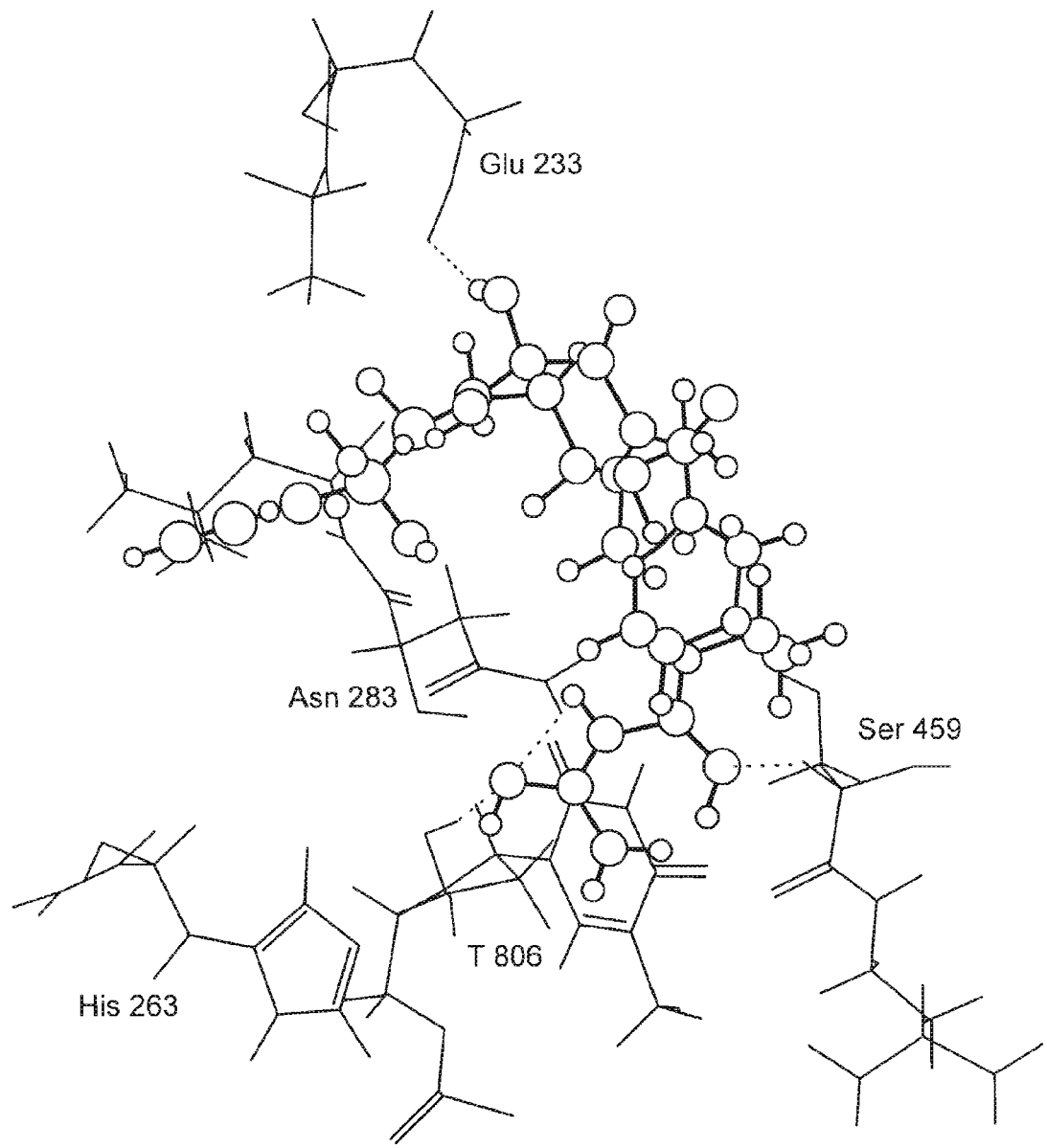
FIG. 3 shows Compounds (a) and (b) (1RHO) (shown in ball-and stick) docked in the binding site of the Tdp1 N domain. Hydrogen bonds are represented as dashed orange lines and contacts as dashed green lines. For clarity, only important residues and atoms are shown. Color codes used: nitrogen—blue, oxygen—red, carbon—black, hydrogen—grey, protein—blue tube, His 263—red.
Figure 3B:
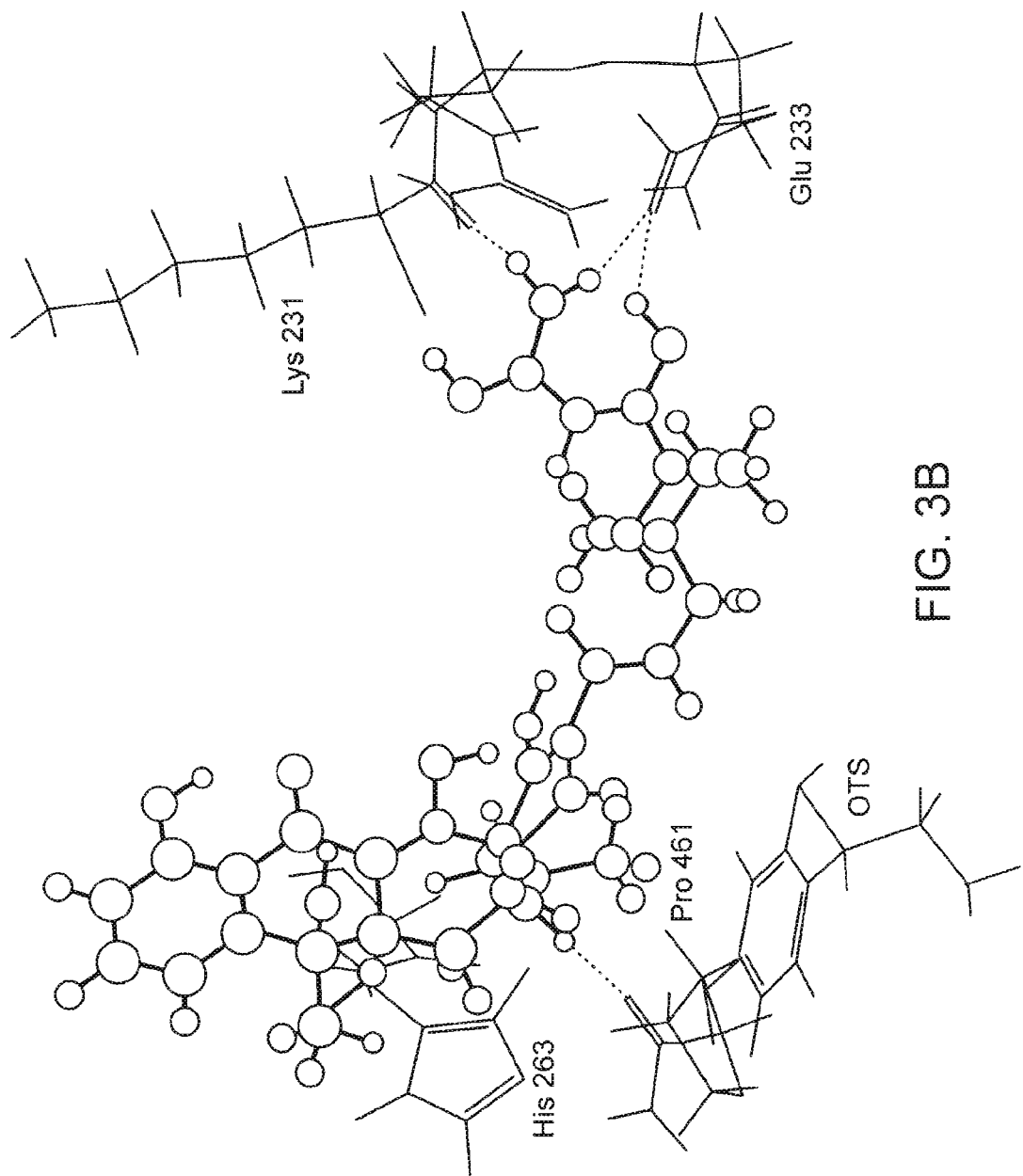
Figure 3C:
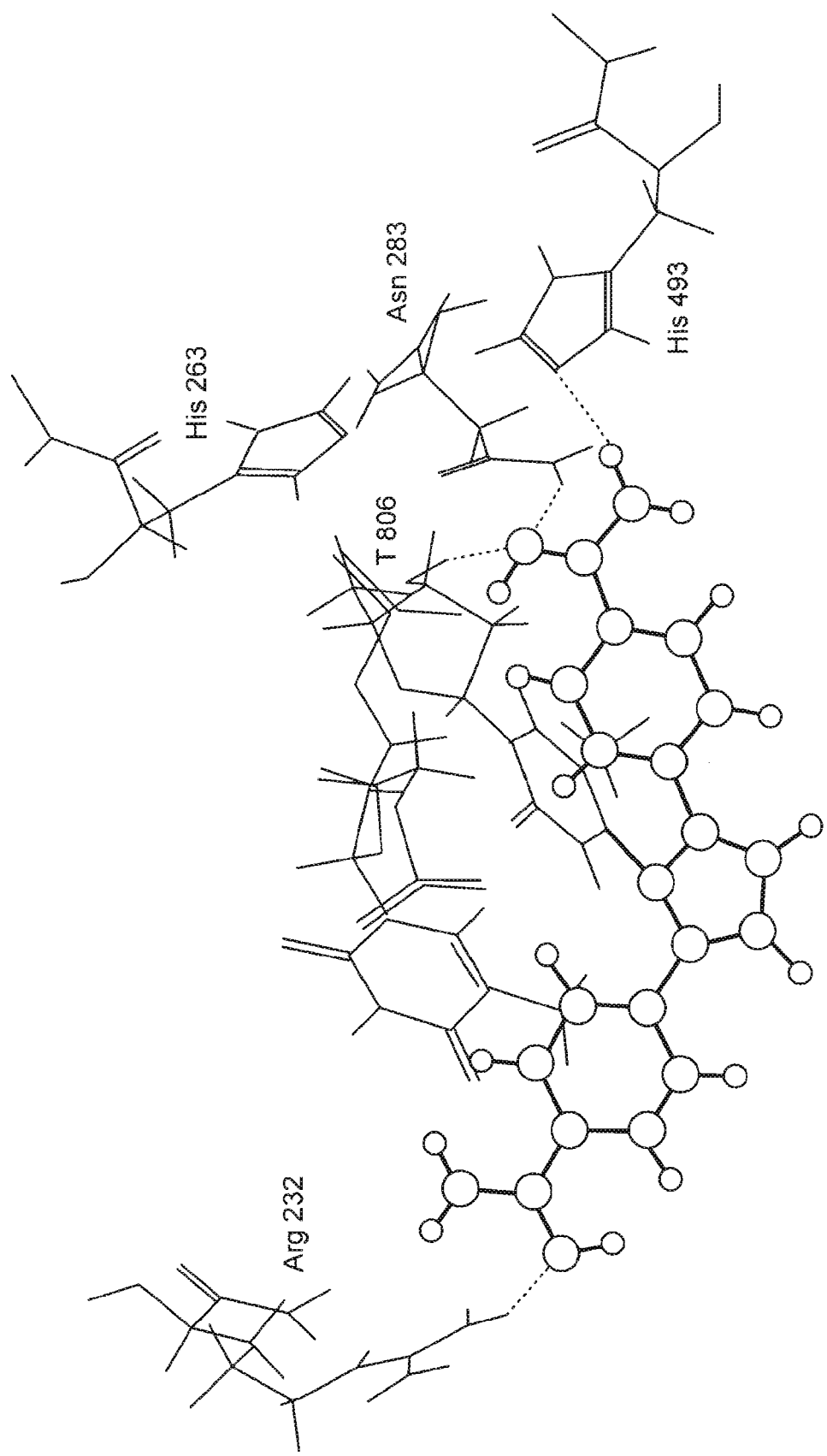
Figure 3D:
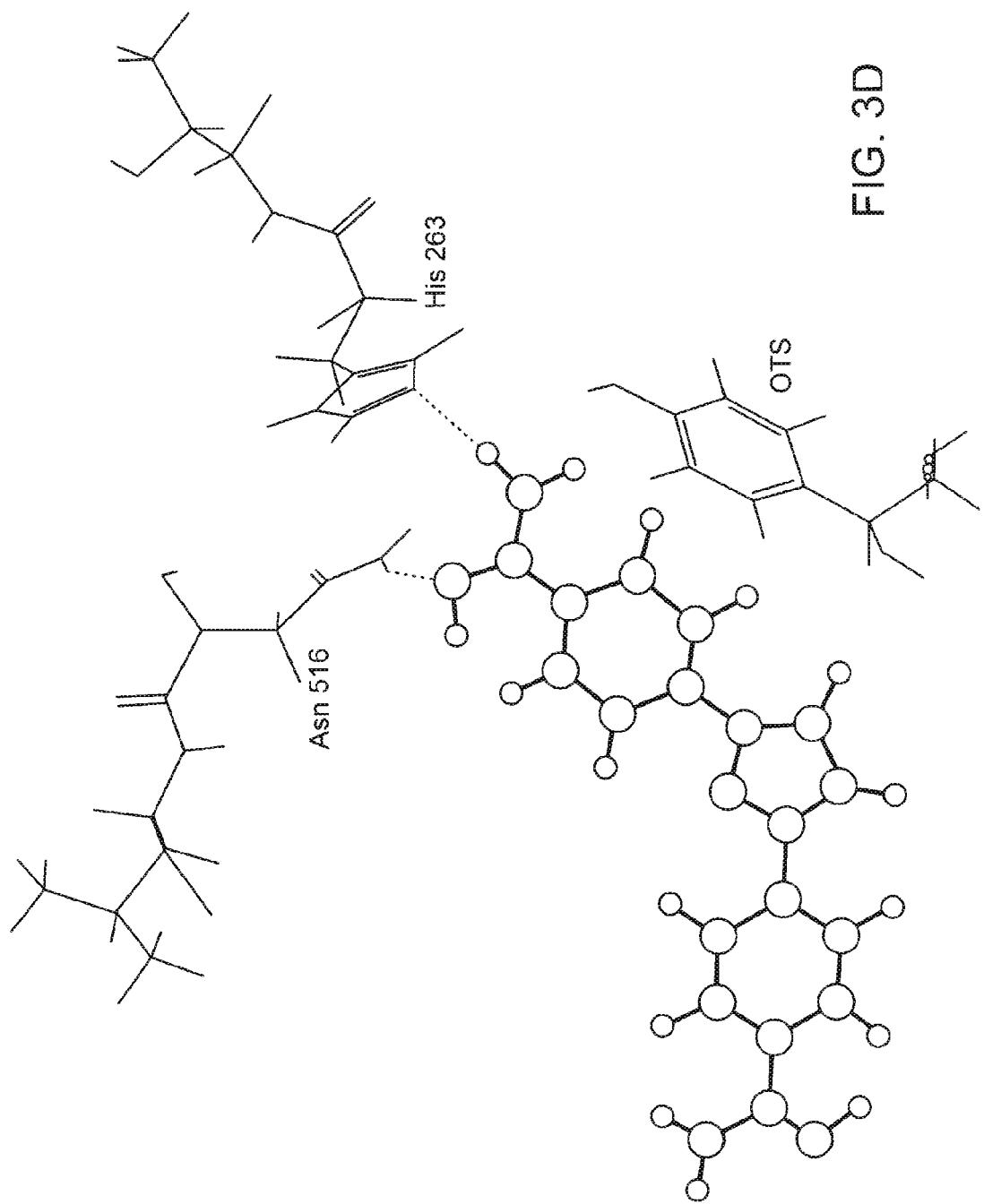

The results are shown in FIGS. 1-3. The docking analysis indicate that in the best poses of Compound (a) (without substrate): the amine group Hydrogen bonds to residue SER 608 (1NOP); hydrogen atom of imine group to His 493 (1RFF); nitrogen atom by C20 contacts with polar hydrogen atom of T 806 of oligonucleotide (1RHO) and in the best poses of Compound (a) (with substrate): oxygen atom of hydroxyl group by C10 and carbonyl group by C11 HBonds to GLY 260, oxygen atom of hydroxyl group by C12 to LYS 720 (1RFF); and the hydrogen atom of hydroxyl group by C12a of NSC 118695 HBonds to PRO 461 (1RHO). In case of Compound (b) (without substrate) hydrogen atom of amine group HBonds to N3 of His 493 (1RHO); nitrogen atom of imine group contacts with T 806 (1RHO), while in crystal structure oxygen atom of VO4 bonds to T 806 of oligonucleotide. When the substrate is present in the active site the amine group contacts with N3 and C4 of His 263 (1NOP); substituent in position 3 contacts with TYR 723 (1RFF); hydrogen atom of amine group contacts to N3 of His 263 (1RHO). The binding model obtained for compound Compound (a) did not show some critical interactions with active sites of Tdp1 N domain. The docking scores correlated poorly with enzyme inhibitory activity, so other approaches were tried to quantify the docked poses. One main reason for the failure to get a good docking mode could be attributed to the size of the molecules and the number of rotatable bonds (13 for Compound (a) and only 4 for Compound (b)).

Example 4

The results obtained in Examples 2 and 3 are used to refine a model for prediction of binding affinity of compounds against Tdp1 as follows. Virtual screening method of compounds obtained from, e.g., the NCI databases such as ChemNavigator based on the biological activity data of confirmed 34 compounds active in the low micromolar range. The obtained compounds will then be subjected to flexible docking as described above, and compounds are selected based on the docking score for the Energy of the Model. The results are compared with a training set of compounds found to bind to the active site of Tdp1.

Example 5

Materials and Methods

Reagents.

Tween-20, KCl, fluorescein isothiocyanate (FITC), and PBS were procured from Sigma-Aldrich. DMSO certified ACS grade was obtained from Fisher. The AlphaScreen FITC/streptavidin detection kit was from PerkinElmer Life and Analytical Sciences (Waltham, Mass.). Assay buffer consisted of PBS, pH 7.4, 80 mM KCl and 0.05% Tween-20. Recombinant Tdp1 was expressed and purified as described elsewhere (Antony et al., *Nucleic Acids Research* 35:4474-4484 (2007). The Sigma-Aldrich LOPAC$^{1280}$ library of 1280 known bioactives was received as DMSO solutions at initial concentration of 10 mM and plated as described elsewhere (Inglese et al., *Proc. Natl. Acad. Sci. USA* 103:11473-11478 (2006); Yasgar et al., *J. Assoc. Lab. Automat.* 13:78-89 (2008)).

AlphaScreen Substrate.

The biotinylated phosphotyrosine deoxyoligonucleotide (5' biotin-GATCTAAAAGACTT-pY) was synthesized, purified, and QC-tested by Midland Certified Reagent Company, Midland, Tex. Standard overnight 4° C. FITC coupling was performed in-house. The FITC-labeled substrate was purified on Biospin-6 desalting columns (Bio-Rad, Hercules, Calif.) and its concentration was determined by UV-vis spectrophotometry.

Assay Development and Optimization.

Assay reaction mixtures and substrate/beads titrations were initially performed at 20 µl final volume in 384-well plates. For the subsequent 1,536-well based experiments, Flying Reagent Dispenser (FRD, Aurora Discovery, presently Beckman-Coulter) was used to dispense reagents into the assay plates, while a pintool was used to deliver DMSO solutions of the test inhibitors. Plates were read on Envision plate reader (PerkinElmer) equipped with AlphaScreen optical detection module. For testing the effect of enzyme reaction conditions on the $IC_{50}$ values for select inhibitors, the respective compounds were prepared as 24-point twofold intra-plate dilution series and assayed as described.

qHTS Protocol and Data Analysis.

Three µl of reagents (buffer in columns 3 and 4 as negative control and 1.33 nM Tdp1 in columns 1, 2, 5-48) were dispensed into 1,536-well black solid bottom plate. Compounds (final concentrations in the range of 0.7 nM to 57 µM) were transferred via Kalypsys pintool equipped with 1,536-pin array. The plate was incubated for 15 min at room temperature, and then 1 µl of substrate (15 nM final concentration) was added to start the reaction. After 5 min incubation at room temperature, 1 µl of bead mix (15 µg/mL final concentration) was added and the plate was further incubated for 10 min at room temperature prior to signal measurement. Substrate and beads were prepared and kept in amber bottles to prevent photo-degradation. Library plates were screened starting from the lowest and proceeding to the highest concentration. Vehicle-only plates, with DMSO being pin-transferred to the entire column 5-48 compound area, were included at the beginning and the end of the screen in order to record any systematic shifts in assay signal. Screening data were corrected, normalized, and curve-fitted by using in-house developed algorithms.

Secondary Assays.

One nanomolar of 5'-$^{32}$P-labeled substrate (N14Y; 5'-GATCTAAAAGACTT-Tyrosine-3') was incubated with 0.1 nM recombinant Tdp1 in the absence or presence of inhibitor for 20 min at 25° C. in a reaction buffer containing 50 mM Tris-HCl (pH 7.5), 80 mM KCl, 2 mM EDTA, and 40 µg/ml BSA. Reactions were terminated by the addition of one volume of gel loading buffer (96% (v/v) formamide, 10 mM EDTA, 1% (w/v) xylene cyanol and 1% (w/v) bromphenol blue). The samples were subsequently heated to 95° C. for 5 min and subjected to 20% denaturing PAGE. When the Tdp1 mutant H493R (100 nM) was employed, the reactions were stopped with one volume of SDS loading dye and analyzed by 4-20% SDS-PAGE. All gels were dried and exposed on a PhosphorImager screen. Imaging and quantification were done using a Typhoon 8600 and ImageQuant software (GE Healthcare, Piscataway, N.J.).

Results

Assay Design.

To configure an assay for Tdp1, we utilized the ability of the AlphaScreen system to report on the integrity of the phosphotyrosine-based substrate, viewed here as a multi-site analyte. The AlphaScreen signal is a direct consequence of the close proximity of donor and acceptor beads, which is achieved by the formation of a ternary donor-analyte-acceptor recognition complex. To realize the AlphaScreen assay using the consensus DNA-pY substrate for Tdp1, 5'GATCTAAAAGACTTpY, recognition elements for both bead types had to be introduced. To this end, we coupled a fluorescein isothiocyanate (FITC) to the amino group of tyrosine in a phosphotyrosine-containing single stranded DNA substrate bearing a biotin at its 5' end. Thus, intact substrate, when mixed with streptavidin-donor and anti-FITC antibody-acceptor beads, was expected to yield a high AlphaScreen signal, while the Tdp1-catalyzed substrate hydrolysis would result in a decreased signal. Conversely, if the Tdp1 catalysis was inhibited, an elevated signal would be observed for that sample.

Assay Set-Up and Optimization in 384-Well Plates.

In a 384-well plate, the addition of an equimolar mix of anti-FITC-acceptor and streptavidin-donor AlphaScreen beads to FITC-DNA substrate generated a strong signal while omission of substrate resulted in background readings. The concentration-response curve of the FITC-DNA substrate titrated against constant bead concentration exhibited a maximum around 15 nM followed by a signal decrease to background levels as the substrate concentration was further increased. The biphasic behavior is characteristic of such polyvalent interactions and in this case was due to the saturation of all available binding sites on the beads and the built-up of bipartite populations of beads saturated exclusively by substrate molecules at the expense of tripartite donor-substrate-acceptor assemblies. The maximum-signal concentration of 15 nM falls below the previously reported Km value of Tdp1 of 80±20 nM, thus ensuring good assay sensitivity with respect to potential inhibitors.

When the same-sequence construct devoid of FITC was tested, a weak and considerably right-shifted signal evolution was noted. While this result points to some non-specific binding, the contribution of the latter to the total signal at the 15 nM point appears to be minimal. Moreover, the Tdp1-induced cleavage of the FITC-DNA substrate, when driven to completion, yielded background signal, thus indicating that the small signal increase observed here was likely due to the interaction between the acceptor bead and the tyrosine moiety. In the presence of increasing concentrations of Tdp1, the FITC-coupled tyrosine group was released, preventing anti-FITC acceptor bead positioning close to the donor bead and subsequently leading to an enzyme-dependent loss of signal. DMSO had no effect on the enzymatic reaction (data not shown). Neomycin and vanadate, two previously described weak Tdp1 inhibitors, both inhibited Tdp1 in this assay. The test method and reaction conditions of the original studies of neomycin and vanadate differ from those used in the present assay; nevertheless, the potencies of the two compounds as determined here were in agreement with these prior publications, with neomycin being a weak low-millimolar inhibitor and vanadate exhibiting its inhibition in the sub-millimolar range.

Assay Optimization in 1536-Well Format and Pilot Screens of the LOPAC[1280] Collection.

The assay was further miniaturized to a final volume of 5 μl in 1,536-well format by direct volume reduction. The inclusion of Tween-20 in the assay buffer helped prevent enzyme absorption to the polystyrene wells and minimized the interfering effect of promiscuous inhibitors acting via colloidal aggregate formation. In order to verify assay integrity over the intended timeline for automated robotic screening, reagent stability over time was assessed by running the assay at multiple time points while storing the working reagents at 4° C. Reagents remained stable for almost 2 days of storage, considerably beyond the overnight period needed for a robotic screen.

To further validate the present assay in a real 1536-well based HTS context, the LOPAC[1280] Library of Pharmacologically Active Compounds was screened in qHTS mode as eight-point concentration series. The pilot screen performed robustly, yielding average Z' factor (Zhang et al., *J. Biomol. Screen.* 4:67-73 (1999)) of 0.71. After data analysis, certain active compounds were selected for further studies.

Hit Validation by Secondary Assays and Mechanistic Studies of Me-3,4-Dephostatin.

Activity of certain compounds was also tested in secondary radiolabel gel-based assays (Inamdar et al., *J. Biol. Chem.* 277:27162-27168 (2002); Davies et al., *J. Mol. Biol.* 324: 917-932 (2002)).

The assays identified several tetracycline and oxytetracycline inhibitors of Tdp1. The structures of certain compounds are shown below:

| Compound | Activity (qHTS) | Activity (Gel) |
|---|---|---|
| | IC50: 0.20 μM | <100 nM? |
| 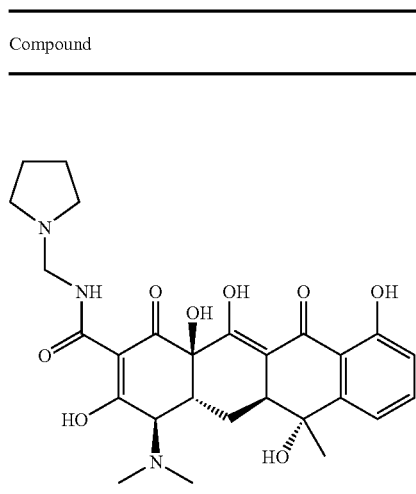 NCGC00013628-01 | IC50: 0.2 μM | 5 μM |
| 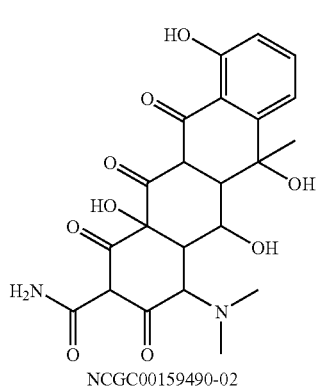 [SMILES: CN(C)C1C(=O)C(C(N)=O)C(=O)C2(O)C(=O)C3C(=O)c4c(O)cccc4C(C)(O)C3C(O)C12] NCGC00159490-02 | IC50: 0.63 μM | 8 μM |
| 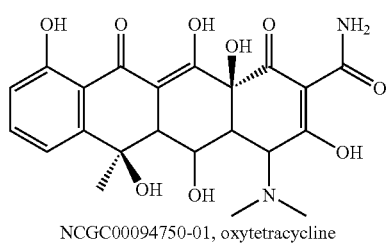 NCGC00094750-01, oxytetracycline | | |

-continued
| Compound | Activity (qHTS) | Activity (Gel) |
|---|---|---|
| 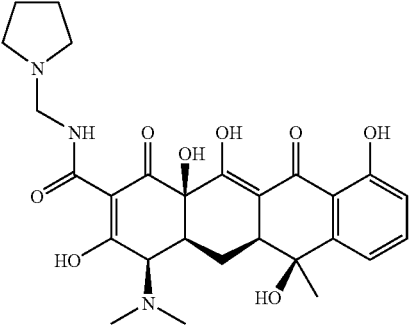<br>NCGC00016537-01, rolitetracycline | IC50: 1.26 μM | 30.2 μM |
| 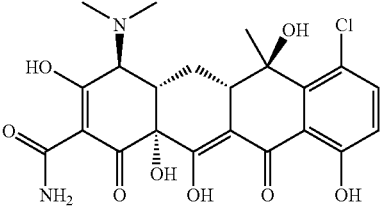<br>NCGC00016289-01, chlortetracycline HCl | IC50: 2.82 μM | 13.2 μM |
| 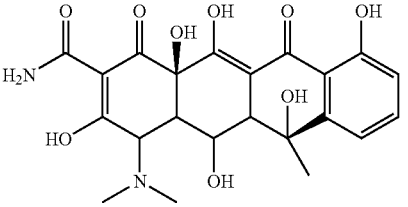<br>NCGC00091268-01, oxytetracycline HCl | IC50: 3.16 μM | 10 μM |
| 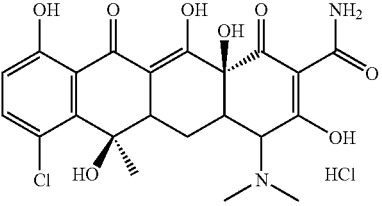<br>NCGC00094615-01, chlortetracycline hydrochloride | IC50: 3.16 μM | 20 μM |
| 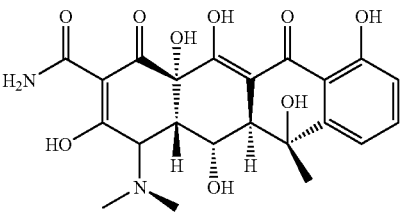<br>NCGC00091268-02 | IC50: 4.47 μM | 3 μM |

-continued
| Compound | Activity (qHTS) | Activity (Gel) |
|---|---|---|
| | IC50: 14.13 μM | 10 μM |
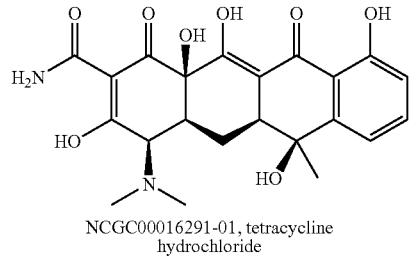 [SMILES: CN(C)[C@H]1C(O)=C(C(N)=O)C(=O)[C@]2(O)C(O)=C3C(=O)c4c(O)cccc4[C@@](C)(O)[C@H]3C[C@@H]12]
NCGC00016291-01, tetracycline hydrochloride
IC50: 10 μM    N/D
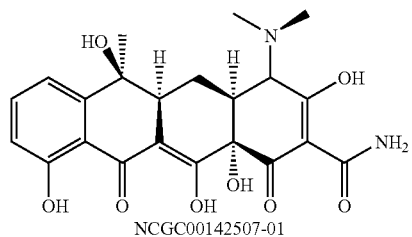
NCGC00142507-01
IC50: 12.59 μM    N/D
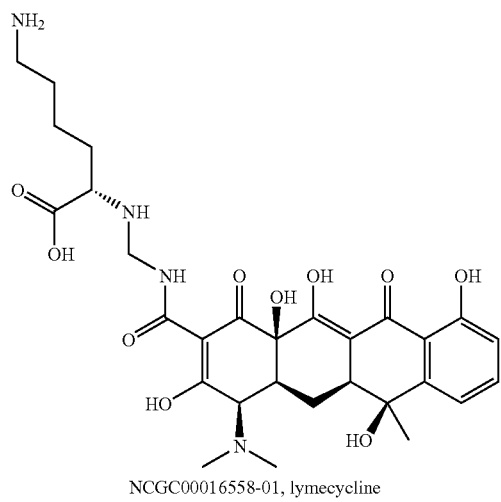 [SMILES: CN(C)[C@H]1C(O)=C(C(=O)NCN[C@@H](CCCCN)C(=O)O)C(=O)[C@]2(O)C(O)=C3C(=O)c4c(O)cccc4[C@@](C)(O)[C@H]3C[C@@H]12]
NCGC00016558-01, lymecycline
IC50: N/D    N/D
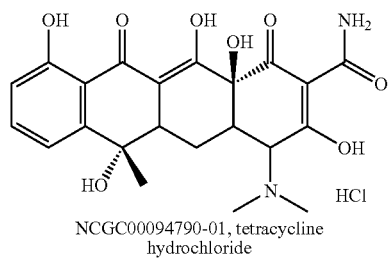
NCGC00094790-01, tetracycline hydrochloride -continued
| Compound | Activity (qHTS) | Activity (Gel) |
|---|---|---|
| 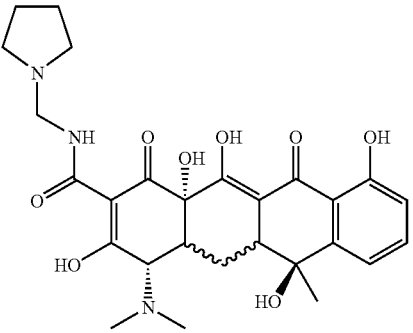  MLS000028710-01 | IC50: 0.71 µM | N/A |
| 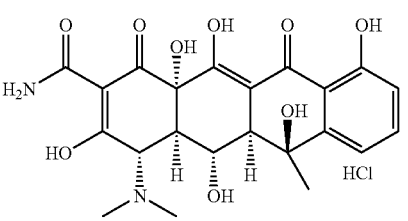  AB07981412-01, oxytetracycline HCl | IC50: 0.50 µM | N/A |
| 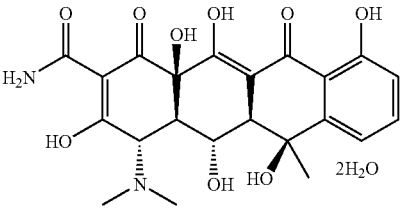  NCGC00017060-01, oxytetracycline dihydrate | IC50: 1.59 µM | N/A |
| 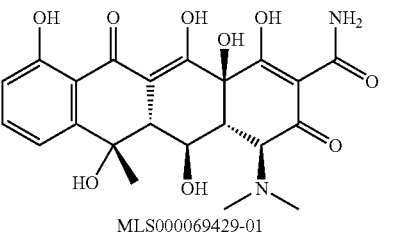 [SMILES: CN(C)[C@@H]1C(=O)C(C(N)=O)=C(O)[C@@]2(O)C(O)=C3C(=O)c4c(O)cccc4[C@@](C)(O)[C@H]3[C@H](O)[C@@H]12]  MLS000069429-01 | IC50: 0.4 µM | N/A |
| 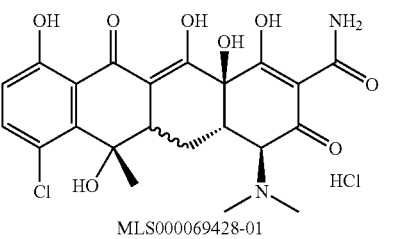  MLS000069428-01 | N/A | N/A |

| Compound | Activity (qHTS) | Activity (Gel) |
|---|---|---|
| 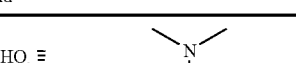 NCGC00161665-01 | N/A | N/A |

N/A = not available
N/D = not detectable

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A method of inhibiting tyrosyl-DNA phosphodiesterase 1 activity in a subject, comprising administering to the subject in need thereof an effective amount of a compound of

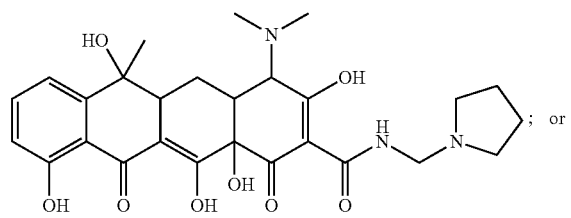; or

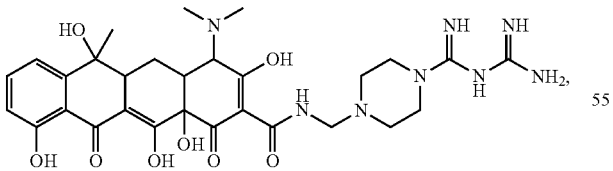

or a combination thereof to inhibit tyrosyl-DNA phosphodiesterase 1 activity,
the method further comprising administering to the subject a Topoisomerase I inhibitor.

2. A method of inhibiting tyrosyl-DNA phosphodiesterase 1 activity in a subject, comprising administering to the subject in need thereof an effective amount of a compound of

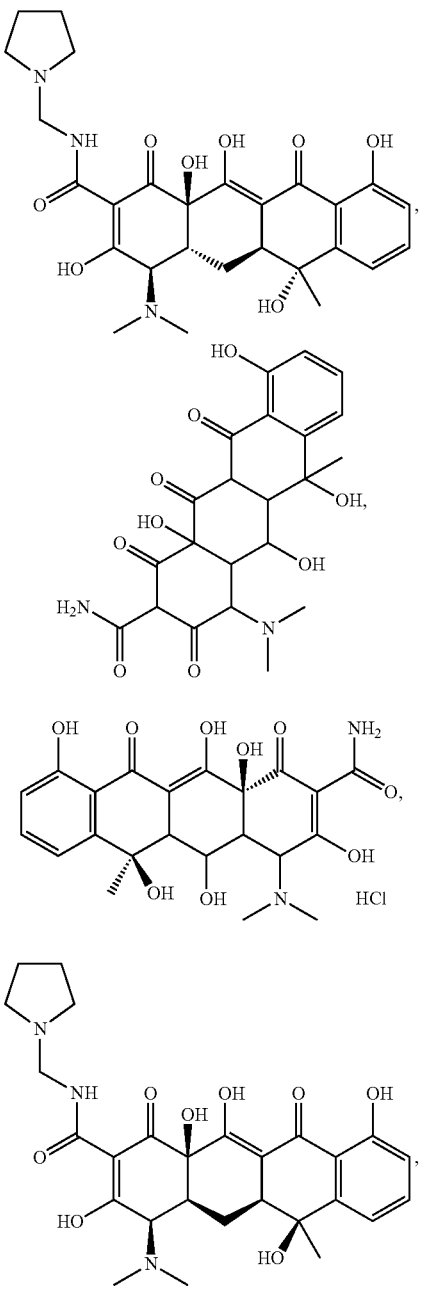

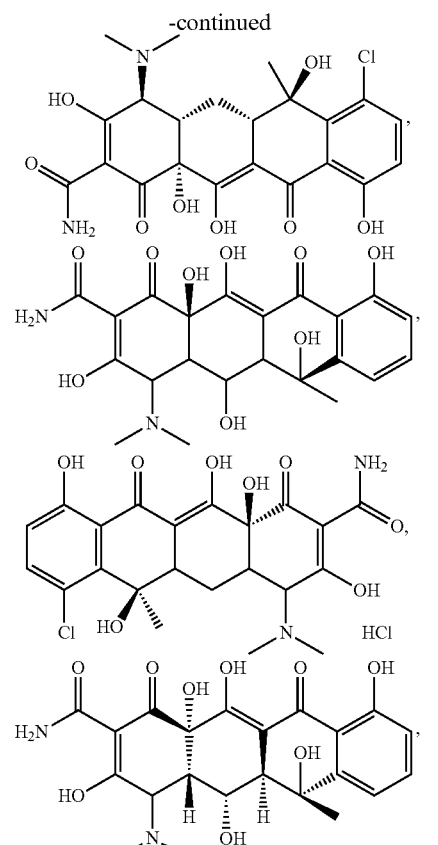

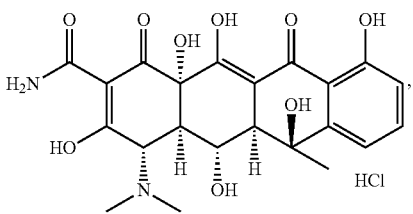

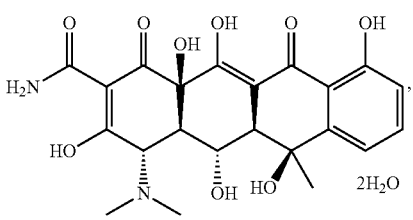

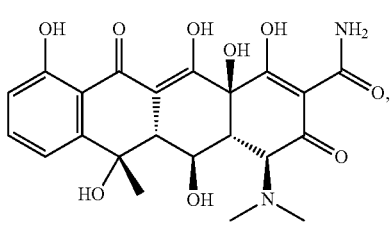

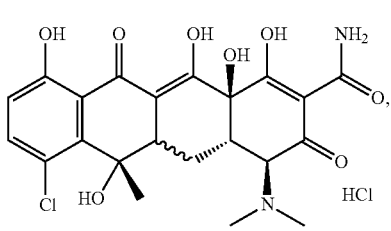

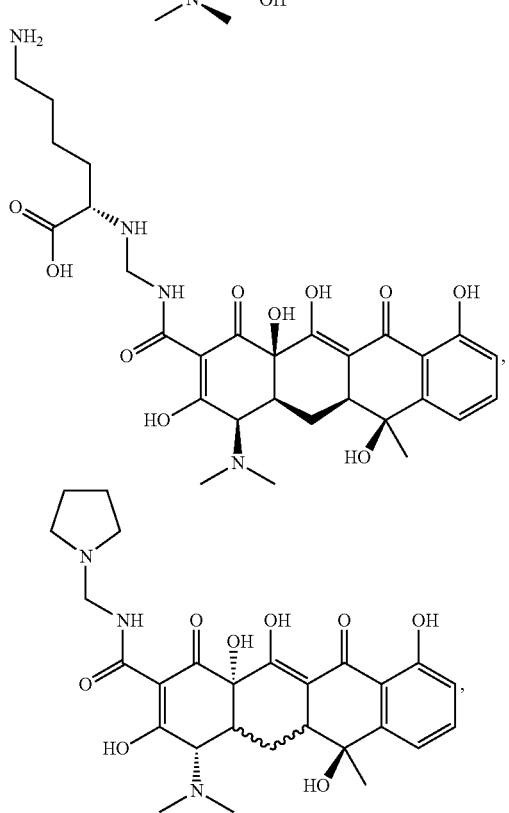

or a combination thereof to inhibit tyrosyl-DNA phosphodiesterase 1 activity, the method further comprising administering to the subject a Topoisomerase I inhibitor.

3. The method of claim 1, wherein the Topoisomerase I inhibitor is camptothecin, irinotecan, topotecan, saintopin, or a derivative or analog thereof.

4. The method of claim 2, wherein the Topoisomerase I inhibitor is camptothecin, irinotecan, topotecan, saintopin, or a derivative or analog thereof.

5. The method of claim 1, wherein the subject is a human.

6. The method of claim 2, wherein the subject is a human.

7. The method of claim 3, wherein the subject is a human.

8. The method of claim 4, wherein the subject is a human.

* * * * *